(12) United States Patent
Gupta et al.

(10) Patent No.: US 12,098,391 B2
(45) Date of Patent: Sep. 24, 2024

(54) GENERATION OF HEPATOCYTES FROM PLURIPOTENT STEM CELLS

(71) Applicant: ALBERT EINSTEIN COLLEGE OF MEDICINE, Bronx, NY (US)

(72) Inventors: Sanjeev Gupta, Scarsdale, NY (US); Sriram Bandi, Belleville, NJ (US)

(73) Assignee: Albert Einstein College of Medicine, Bronx, NY (US)

( * ) Notice: Subject to any disclaimer, the term of this patent is extended or adjusted under 35 U.S.C. 154(b) by 602 days.

(21) Appl. No.: 16/360,228

(22) Filed: Mar. 21, 2019

(65) Prior Publication Data

US 2019/0390163 A1    Dec. 26, 2019

Related U.S. Application Data

(60) Continuation of application No. 15/900,834, filed on Feb. 21, 2018, now Pat. No. 10,287,552, which is a division of application No. 14/409,234, filed as application No. PCT/US2013/048113 on Jun. 27, 2013, now abandoned.

(60) Provisional application No. 61/666,219, filed on Jun. 29, 2012.

(51) Int. Cl.
*C12N 5/071*    (2010.01)
*A61K 35/407*    (2015.01)

(52) U.S. Cl.
CPC ............ *C12N 5/067* (2013.01); *A61K 35/407* (2013.01); *C12N 5/0672* (2013.01); *C12N 2500/84* (2013.01); *C12N 2501/999* (2013.01); *C12N 2502/14* (2013.01); *C12N 2506/02* (2013.01)

(58) Field of Classification Search
CPC ............ A61K 35/407; C12N 2506/02; C12N 2501/999
USPC ........................................................ 435/377
See application file for complete search history.

(56) References Cited

U.S. PATENT DOCUMENTS

| 8,148,151 B2 | 4/2012 | Zhao et al. |
| 2009/0181453 A1 | 7/2009 | Keller et al. |
| 2011/0250686 A1 | 10/2011 | Heins et al. |
| 2011/0311977 A1 | 12/2011 | Mandal et al. |

OTHER PUBLICATIONS

Van der Garde (2015, Stem Cells and Development, 24:2649-2659.*
Hrvatin (2014, PNAS, 111:3038-3043).*
PCT International Search Report and Written Opinion, dated Nov. 27, 2013 in connection with PCT International Application No. PCT/US2013/48113, 11 pages.
Tanaka (2009, Mechanisms of Development, 126:665-676).
Duerholt (2009, BMC Biotechnology, 9:89 pp. 1-15).
Chung (2002 Archives of Biochemistry and Biophysics, 408:147-154).
Hwang (2006, Tissue Engineering, 12:1381-1392).
Van Der Valk (2010, Toxicology in vitro, 24: 1053-1063).
Keller, Genes and Development, 2005, 19:1129-1155.

* cited by examiner

*Primary Examiner* — Valarie E Bertoglio
(74) *Attorney, Agent, or Firm* — Foley Hoag LLP; Erik A. Huestis; Thi K. Dio

(57) ABSTRACT

Methods are provided for producing differentiated cells from stem cells, including producing hepatocytes. Compositions thereof are also provided, as are methods of treating a liver disorder.

19 Claims, 10 Drawing Sheets

Specification includes a Sequence Listing.

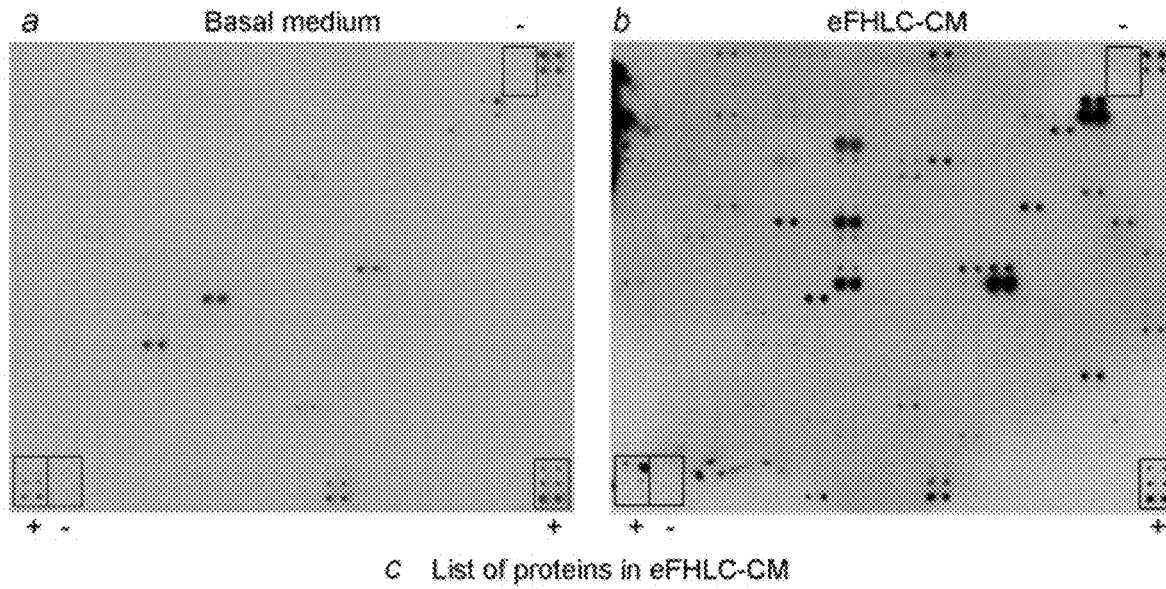

c List of proteins in eFHLC-CM

| | |
|---|---|
| Activated leukocyte cell adhesion molecule | Interleukin-12 Receptor beta 2 |
| Angiostatin | Interleukin-17 Receptor C |
| Factor III | Interleukin-17 Receptor D |
| Ectodysplasin-A2 | Interleukin-23 |
| Endothelial monocyte activating protein-II | Interleukin-27 |
| Endostatin | Lymphocyte-specific protein tyrosine kinase |
| ErbB3 | Latent Transforming growth factor-beta |
| Fibroblast growth factor 16 | Lipopolysaccharide binding protein |
| Follistatin-like 1 | Monocyte chemoattractant protein-1 |
| Galectin3 | Matrix metallopeptidase 9 |
| Granulocyte colony stimulating factor | Matrix metallopeptidase 10 |
| Growth differentiation factor 3 | Neurotrophin 4 |
| Growth differentiation factor 5 | Platelet-derived growth factor |
| Growth differentiation factor 9 | Progranulin |
| Growth differentiation factor 15 | Secreted Frizzled related protein 4 |
| Tumor necrosis factor receptor superfamily member 18 | Soluble glycoprotein130 |
| Glypican3 | Secreted protein acidic and rich in cysteine |
| GREMLIN | Tissue factor pathway inhibitor |
| Intercellular adhesion molecule 1 | Transforming growth factor-beta receptor I |
| Intercellular adhesion molecule 2 | Thrombospondin-2 |
| Insulin-like growth factor binding protein 2 | Tissue inhibitor metalloproteinases 1 |
| Insulin-like growth factor binding protein 3 | Tumor necrosis factor receptor I |
| Insulin-like growth factor binding protein 6 | Tumor necrosis factor-like weak inducer of apoptosis receptor protein |
| Insulin-like growth factor-I | Urokinase plasminogen activator |
| Insulin-like growth factor-II Receptor | Urokinase plasminogen activator receptor |
| Interleukin-1 alpha | Vasorin |
| Interleukin-1 beta | Vascular endothelial growth factor |

Fig. 5A-5C

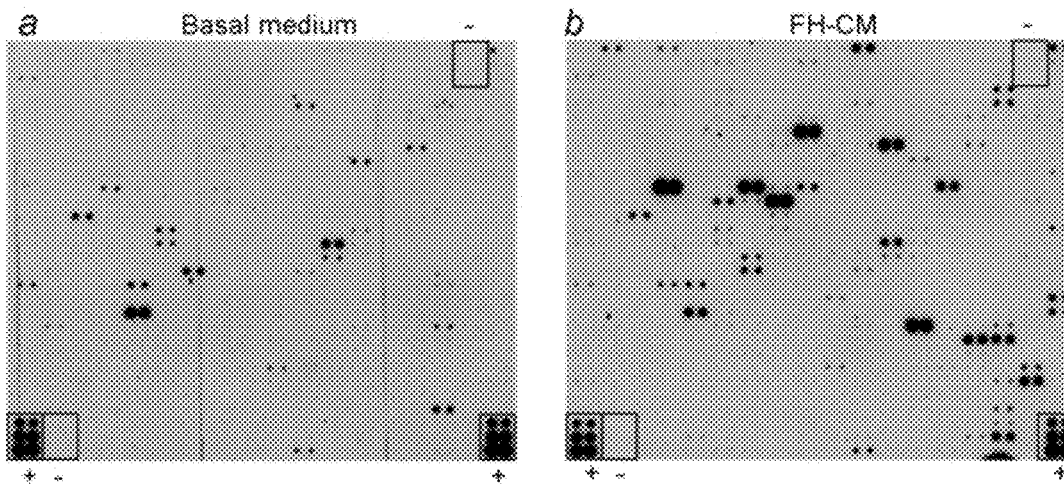

c List of proteins in FH-CM

| HIGHEST | Follistatin |
|---|---|
| Growth regulated protein alpha | Follistain-like 1 |
| Insulin-like growth factor binding protein 7 | Growth differentiation factor 1 |
| Interleukin 8 | Growth differentiation factor 3 |
| HIGH | Growth differentiation factor 5 |
| Galectin 3 | Growth differentiation factor 9 |
| Latent transforming growth factor binding protein 1 | Growth differentiation factor 11 |
| Monocyte chemotactic protein 1 | Growth differentiation factor 15 |
| Osteoprotegerin | Tumor necrosis factor (ligand) superfamily, member 18 |
| Prolactin | Chemokine (C-C motif) ligand 16 |
| SMAD4 | Insulin-like growth factor binding protein 2 |
| Tissue inhibitor of metalloproteinase 1 | Insulin-like growth factor binding protein 3 |
| Ubiquitin+1 | Insulin-like growth factor binding protein 4 |
| Urokinase plasminogen activator | Insulin-like growth factor binding protein 6 |
| MEDIUM | Insulin-like growth factor 2 receptor |
| Chemokine (C-C motif) receptor 3 | Interleukin 11 |
| Decorin | Interleukin 15 receptor alpha |
| Glypican 5 | Interleukin 17 receptor C |
| Interleukin 8 | Interleukin 20 receptor beta |
| Pentraxin 3 | Interleukin 23 |
| Thrombospondin 1 | Matrix metalloproteinase 9 |
| Tissue inhibitor of metalloproteinase 2 | Nephroblastoma overexpressed protein |
| Vascular endothelial growth factor | Preadipocyte factor 1 |
| LOW | Progranulin |
| Activin A | P-selectin |
| Angiogenin | SMAD5 |
| Angiopoietin-like 2 | Neuregulin 1 |
| Endothelial monocyte activated polypeptide 2 | Transforming growth factor, beta receptor 1 |
| Entostatin | Thrombospondin 2 |
| Eotaxin | Transmembrane protein with EGF-like and two follistatin-like domains 1 |
| Erythropoietin | Tumor necrosis factor receptor 1 |
| Fibroblast growth factor 12 | Tumor necrosis factor receptor superfamily, member 10c, decoy without an intracellular domain |
| Fibroblast growth factor 16 | Vascular endothelial growth factor C |

Fig. 6A-6C

SEQUENCE LISTING

```
<160> NUMBER OF SEQ ID NOS: 24

<210> SEQ ID NO 1
<211> LENGTH: 25
<212> TYPE: DNA
<213> ORGANISM: ARTIFICIAL SEQUENCE
<220> FEATURE:
<223> OTHER INFORMATION: PRIMER DIRECTED TO HUMAN OCT4 GENE

<400> SEQUENCE: 1
gacaacaatg aaaatcttca ggaga                                         25

<210> SEQ ID NO 2
<211> LENGTH: 23
<212> TYPE: DNA
<213> ORGANISM: ARTIFICIAL SEQUENCE
<220> FEATURE:
<223> OTHER INFORMATION: PRIMER DIRECTED TO HUMAN OCT4 GENE

<400> SEQUENCE: 2
ttctggcgcc ggttacagaa cca                                           23
```

<210> SEQ ID NO 3
<211> LENGTH: 24
<212> TYPE: DNA
<213> ORGANISM: ARTIFICIAL SEQUENCE
<220> FEATURE:
<223> OTHER INFORMATION: PRIMER DIRECTED TO HUMAN ALB GENE

<400> SEQUENCE: 3
tgcttgaatg tgctgatgac aggg                                    24

<210> SEQ ID NO 4
<211> LENGTH: 25
<212> TYPE: DNA
<213> ORGANISM: ARTIFICIAL SEQUENCE
<220> FEATURE:
<223> OTHER INFORMATION: PRIMEER DIRECTED TO HUMAN ALB GENE

<400> SEQUENCE: 4
aaggcaagtc agcaggcatc tcatc                                   25

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: PRIMER DIRECTED TIO HUMAN AFP GENE

<400> SEQUENCE: 5
tgcagccaaa gtgaagaggg aaga                                    24

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: PRIMER DIRECTED TO HUMAN AFT GENE

<400> SEQUENCE: 6
catagcgagc agcccaaaga agaa                                    24

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CK-19 GENE

<400> SEQUENCE: 7
atggccgagc agaaccggaa                                         20

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CK-19 GENE

<400> SEQUENCE: 8
ccatgagccg ctggtactcc                                         20

<210> SEQ ID NO 9
<211> LENGTH: 17
<212> TYPE: DNA
<213> ORGANISM: ARTIFICIAL SEQUENCE
<220> FEATURE:

```
<223> OTHER INFORMATION: PRIMER DIRECTED TO HUMAN VIM GENE

<400> SEQUENCE: 9
cacctacagc ctctacg                                                   17

<210> SEQ ID NO 10
<211> LENGTH: 16
<212> TYPE: DNA
<213> ORGANISM: ARTIFICIAL SEQUENCE
<220> FEATURE:
<223> OTHER INFORMATION: PRIMER DIRECTED TO HUMAN VIM GENE

<400> SEQUENCE: 10
agcggtcatt cagctc                                                    16

<210> SEQ ID NO 11
<211> LENGTH: 19
<212> TYPE: DNA
<213> ORGANISM: ARTIFICIAL SEQUENCE
<220> FEATURE:
<223> OTHER INFORMATION: PRIMER DIRECTED TO HUMAN ALPHA-SMA GENE

<400> SEQUENCE: 11
agtacccgat agaacatgg                                                 19

<210> SEQ ID NO 12
<211> LENGTH: 16
<212> TYPE: DNA
<213> ORGANISM: ARTIFICIAL SEQUENCE
<220> FEATURE:
<223> OTHER INFORMATION: PRIMER DIRECTED TO HUMAN ALPHA-SMA GENE

<400> SEQUENCE: 12
ttttctcccg gttggc                                                    16

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP1B1 GENE

<400> SEQUENCE: 13
caccaaggct gagacagtga                                                20

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP1B1 GENE

<400> SEQUENCE: 14
gccaggtaaa ctccaagcac                                                20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP2C9 GENE

<400> SEQUENCE: 15
ggacagagac gacaagcaca                                                20
```

```
<210> SEQ ID NO 16
<211> LENGTH: 19
<212> TYPE: DNA
<213> ORGANISM: ARTIFICIAL SEQUENCE
<220> FEATURE:
<223> OTHER INFORMATION: PRIMER DIRECTED TO HUMAN CYP2C9 GENE

<400> SEQUENCE: 16
tggtggggag aaggtcaat                                                19

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP3A4 GENE

<400> SEQUENCE: 17
tgtgcctgag aacaccagag                                               20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP3A4 GENE

<400> SEQUENCE: 18
gcagaggagc caaatctacc                                               20

<210> SEQ ID NO 19
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP2E1 GENE

<400> SEQUENCE: 19
ccgcaagcat tttgactaca                                               20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP2E1 GENE

<400> SEQUENCE: 20
gctccttcac cctttcagac                                               20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP1A1 GENE

<400> SEQUENCE: 21
aggcttttac atccccaagg                                               20

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CYP1A1 GENE
```

```
<400> SEQUENCE: 22
gcaatggtct caccgataca                                               20

<210> SEQ ID NO 23
<211> LENGTH: 19
<212> TYPE: DNA
<213> ORGANISM: ARTIFICIAL SEQUENCE
<220> FEATURE:
<223> OTHER INFORMATION: PRIMER DIRECTED TO HUMAN BETA-ACTIN

<400> SEQUENCE: 23
tcaccaccac ggccgagcg                                                19

<210> SEQ ID NO 24
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN BETA-ACTIN

<400> SEQUENCE: 24
tctccttctg catcctgtcg                                               20
```

GENERATION OF HEPATOCYTES FROM PLURIPOTENT STEM CELLS

CROSS-REFERENCE TO RELATED APPLICATIONS

This application is a Continuation of U.S. patent application Ser. No. 15/900,834, filed Feb. 21, 2018, which is a Divisional of U.S. patent application Ser. No. 14/409,234, filed Dec. 18, 2014, which is a U.S. national stage entry under 35 U.S.C. § 371 of PCT International Patent Application No. PCT/US2013/048113, filed Jun. 27, 2013, which in turn claims the benefit of U.S. Provisional Patent Application No. 61/666,219, filed Jun. 29, 2012, the contents of each of which are incorporated herein by reference into the subject application.

STATEMENT OF GOVERNMENT SUPPORT

This invention was made with government support under grant numbers DK071111, DK088561, DK41296 and CA13330 awarded by the National Institutes of Health. The government has certain rights in the invention.

BACKGROUND OF THE INVENTION

Throughout this application various publications are referred to in parentheses by number. Full citations for these references may be found at the end of the specification. The disclosures of each of these publications, and of all patents, patent application publications and books cited herein, are hereby incorporated by reference in their entirety into the subject application to more fully describe the art to which the subject invention pertains.

The liver occupies a central position in life due to its crucial metabolic, synthetic, storage, and drug or toxin disposal functions. Isolated liver cells are extremely useful for developing disease models, as well as for toxicological testing and drug development. Moreover, because many proteins are made in liver cells, cell/gene therapy directed at the liver is of extensive interest for a long list of genetic or acquired conditions. However, shortages of donor organs have proved to be an insurmountable hurdle for therapeutic and other applications of liver cells. Therefore, alternative means to generate hepatocytes, e.g., from pluripotent stem cells, is of great interest. This requires understanding into the processes by which pluripotent stem cells may transition and differentiate, first into immature and then into mature hepatocytes. Among candidate pluripotent stem cells of interest, human embryonic stem cells (hESC) or induced pluripotent stem cells (iPS), which share properties of the former, divide indefinitely and may differentiate to produce mature cells of various tissues and organs. However, available differentiation protocols to generate hepatocytes from hESC or iPS, etc., are inefficient and generate cells of indeterminate developmental or maturational stages. For instance, the convention of generating hepatocytes from aggregation of hESC or other types of pluripotent stem cells to form embryoid bodies is not only inefficient, but yields complex lineage mixtures at various developmental stages or maturity that pose difficulties in isolating cells of interest, which may be additionally altered or damaged by cell separation procedures (1). Directed differentiation of stem cells into hepatocytes could overcome these problems, (2, 3), but this accomplishment has generally been elusive.

The present invention addresses the need for directed differentiation of stem cells into hepatocytes.

SUMMARY OF THE INVENTION

A method of producing a differentiated cell from a pluripotent stem cell is provided, the method comprising maintaining the pluripotent stem cell in a medium comprising conditioned medium from immortalized fetal hepatoblasts, for a time sufficient to produce the differentiated cell.

A composition is provided for differentiating stem cells into a differentiated cell of interest, the composition comprising conditioned medium obtained from a culture of hepatoblasts cultured in a medium comprising a basal medium.

A composition is provided for differentiating stem cells into a differentiated cell of interest, the composition comprising components identified in conditioned medium obtained from a culture of human fetal hepatoblasts cultured in a medium comprising a basal medium without those components.

A method is provided for treating a liver disorder in a subject comprising administering to the subject an amount of the described compositions, or an amount of the described differentiated cells, in an amount effective to treat a liver disorder.

This indicated that eFHLC were closer to hESC compared with FH-PP. Table in 3C provides the overall distribution of differentially expressed genes and fractions representing major gene ontology groups and Kyoto Encyclopedia of Genes and Genomes (KEGG) pathways. Changes in TGF-β signaling and BMP signaling in eFHLC were observed compared with FH-PP cells. The data indicated TGF-β and BMP signaling were more active in eFHLC. This was in agreement with similar findings after FH-PP had been cultured.

FIG. 4A-4F. Secretory, synthetic, metabolic and hepatoprotective functions in cultured eFHLC. (A-C) Studies with hESC, d14 eFHLC and HepG2 hepatoma cells for albumin secretion, urea synthesis and CYP450 activity showing gain of these functions in eFHLC. (D) Assay of TNF-α cytotoxicity in primary mouse hepatocytes showing eFHLC-CM protected cells. Asterisks indicate $p<0.05$ versus hESC (A-C), or untreated controls (D). (E-F) Show regulation of ataxia telangiectasia mutated (ATM) signaling in cells. After 15 μM cis-P, a known inducer of double-strand DNA breaks, viability of ATMP-tdT Huh-7 cells, declined (C) and ATM promoter activity increased (D), confirming DNA damage-induced ATM signaling. When cells were treated with cis-P plus FGF1, FGF2, GCSF and IGF1, cell viability improved and ATM promoter activity decreased. VEGF was ineffective. Asterisks, $p<0.05$, versus cis-P-treated cells.

FIG. 5A-5C. RayBiotech array analysis of 507 proteins in eFHLC-CM. (A) Basal medium not exposed to cells. (B) eFHLC-CM harvested after 24 h. Boxes marked by (+) and (−) in A and B indicate positive and negative controls. Each protein was represented twice in arrays. (C) Proteins found in eFHLC-CM are listed.

FIG. 6A-6C. RayBiotech array analysis of proteins in FH-CM. (A) Shows basal medium containing various additives but without exposure to cells. (B) FH-CM harvested after 24 h. Boxes marked by (+) and (−) in A and B indicate positive and negative array controls. Each protein was represented twice in arrays. (C) Shows categorization of proteins in FH-CM according to density of array spots to indicate higher or lower levels.

FIG. 7A-7D. RayBiotech array analysis of receptor tyrosine kinase (RTK) expression in undifferentiated hESC. (A) Untreated control hESC with basal phosphorylation of several receptor tyrosine kinases (RTKs). (B and C) hESC stimulated for 1 h (B) or 6 h (C) with FH-CM before analysis of phosphorylated RTKs. Data showed no differences from untreated controls in (A). Each protein was spotted twice. Boxes marked by (+) and (−) in A-C indicate positive and negative array controls. (D) List of phosphorylated RTKs in hESC irrespective of basal or FH-CM-stimulated conditions.

Figures 8A, 8B:
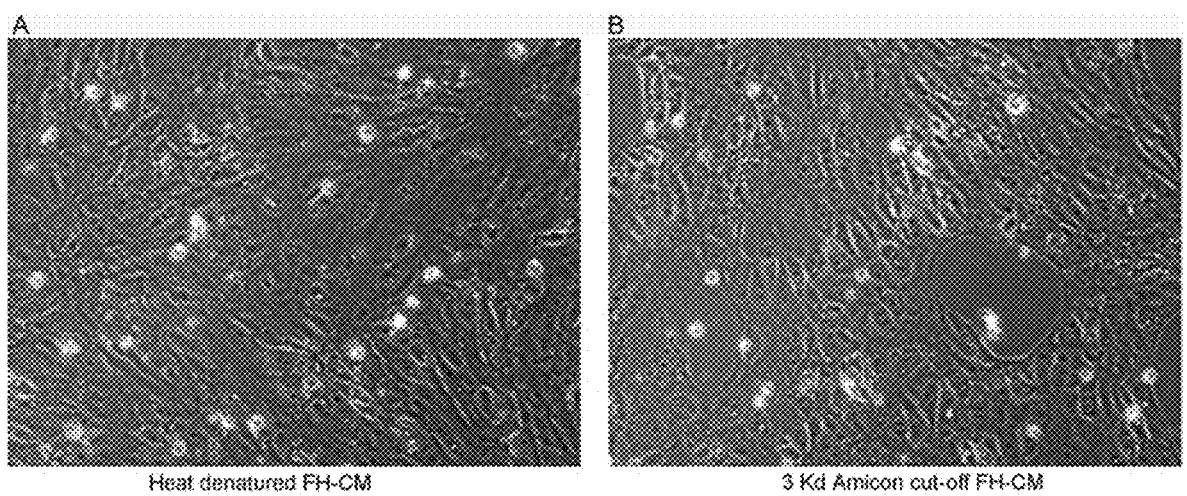

FIG. 8A-8B. Differentiation of hESC over 3 d with FH-CM altered by protracted heating to degrade proteins or passage through Amicon membrane of 3 Kd cut-off size. (A) hESC after culture with heat denatured FH-CM showing switch to epithelial morphology. (B) hESC cultured with FH-CM passed through Amicon membrane showing epithelial morphology. Orig. Mag., ×100.

FIG. 9A-9F. Hepatic differentiation of hESC with group of 7 CP. Panels on left show undifferentiated hESC, panels in middle show hESC cultured with FH-CM and panels on right show hESC cultured with combination of 7 CP, which were most effective for this purpose. (A) Phase contrast microscopy showing undifferentiated hESC with small size of cells (left), whereas hESC cultured with FH-CM (middle) or 10 μm amounts of 7 CP showed larger size and epithelial morphology (on right). (B-D) Immunofluorescence staining of hESC under conditions indicated for OCT4, albumin and vimentin. This showed loss of OCT4 and gain of albumin and vimentin expression after differentiation (red color). Nuclei were stained blue with DAPI. (E & F) eFHLC derived from hESC by either FH-CM or CP showed urea synthesis (E) as well as cytochrome P450 activity with conversion of ethoxyresorufin to resorufin (E). Human HepG2 cells were included for comparisons in E & F.

FIG. 10A-10F. Hepatic differentiation of iPSC with group of 7 CP. Panels on left show undifferentiated iPSC, panels in middle show iPSC cultured with FH-CM and panels on right show iPSC cultured with combination of 7 CP, which were most effective. (A) Phase contrast microscopy showing undifferentiated iPSC with small size of cells (left), whereas iPSC cultured with FH-CM (middle) or 10 μm amounts of 7 CP showed larger size and epithelial morphology (on right). (B-D) Immunofluorescence staining of iPSC under conditions indicated for OCT4, albumin and vimentin. This showed loss of OCT4 and gain of albumin and vimentin expression after differentiation (red color). Nuclei were stained blue with DAPI. (E & F) eFHLC derived from iPSC by either FH-CM or CP showed urea synthesis (E) as well as cytochrome P450 activity with conversion of ethoxyresorufin to resorufin. (F) Human HepG2 cells were included for comparisons in E & F.

DETAILED DESCRIPTION OF THE INVENTION

A method of producing a differentiated cell from a pluripotent stem cell is provided, the method comprising maintaining the pluripotent stem cell in a medium comprising isolated conditioned medium from hepatoblasts, for a time sufficient to produce the differentiated cell.

A method of producing a differentiated cell from a pluripotent stem cell is provided, the method comprising maintaining the pluripotent stem cell in a medium comprising isolated conditioned medium from fetal hepatoblasts, for a time sufficient to produce the differentiated cell.

Also provided is a method of producing a differentiated cell from a pluripotent stem cell, the method comprising maintaining the pluripotent stem cell in a medium comprising conditioned medium from hepatoblasts, or a medium comprising two or more of phenacetin, phytosphingosine HCl, and pyridoxal HCl, for a time sufficient to produce the differentiated cell. In a preferred embodiment, the method comprises maintaining the pluripotent stem cell in a medium comprising two or more of phenacetin, phytosphingosine HCl, and pyridoxal HCl.

In an embodiment of the methods, the differentiated cell is a hepatocyte. In an embodiment, the differentiated cell exhibits a meso-endodermal phenotype of a fetal human hepatocyte. In an embodiment, the differentiated cell exhibits ureagenesis and/or albumin synthesis and/or vimentin expression. In an embodiment, the pluripotent stem cell is an inducible pluripotent stem cell or is an embryonic stem cell.

In an embodiment of the methods, the hepatoblasts are immortalized. In an embodiment, the hepatoblasts have been immortalized by contact with a telomerase. In an embodiment, the hepatoblasts have been immortalized by expression of telomerase, or maintenance of telomerase expression. In an embodiment, hepatoblasts are human. In an embodiment, hepatoblasts are fetal. In an embodiment, hepatoblasts are immortalized human fetal hepatoblasts. In an embodiment, hepatoblasts are isolated. In an embodiment, the medium does not comprise serum. In an embodiment, the conditioned medium from immortalized human fetal hepatoblasts comprises medium obtained from a culture of immortalized human fetal hepatoblasts cultured in a medium comprising a basal medium. In an embodiment, the immortalized fetal hepatoblasts are human immortalized fetal hepatoblasts. In an embodiment, the hepatoblasts are mammalian, but are not human. In an embodiment, the hepatoblasts are human, but are not fetal. In an embodiment, the medium comprising a basal medium further comprises L-glutamine, one or more non-essential amino acids, and an antibiotic. In an embodiment, the basal medium is a Dulbecco's Modified Eagle's Medium (DMEM). In an embodiment, the antibiotic is penicillin-streptomycin. In an embodiment, the non-essential amino acids are glycine, L-alanine, L-asparagine, L-aspartic acid, L-glutamic acid, L-proline and L-serine. In an embodiment, the medium comprising a basal medium further comprises an artificial serum replacement.

A conditioned medium, with regard a culture, is a medium in which the cell culture has been maintained. In an embodiment, the conditioned medium has been exposed to the cells being cultured for 1 or more hours, 2 or more hours, 6 or more hours, 12 or more hours, 24 or more hours, one week or more or two weeks or more.

In an embodiment of the methods, the medium further comprises one or more of L-cysteinglutathione disulfide, γ-Glu-Cys, DL-kynurenine, D-penicillamine disulfide, and tetracaine HCl. In an embodiment, the medium does not comprise tetracaine HCl. In an embodiment, the medium comprises L-cysteinglutathione disulfide, γ-Glu-Cys, DL-kynurenine, D-penicillamine disulfide, phenacetin, phytosphingosine HCl, and pyridoxal HCl.

In an embodiment of the methods, the medium comprises retinoic acid and/or dexamethasone. In an embodiment, the medium comprises L-glutamine. In an embodiment, the medium comprises a selenium compound. In an embodiment, the medium comprises sodium selenite. In an embodiment, the medium comprising a selenium compound also comprises one or more of an albumin, transferrin, insulin, progesterone, putrescine, biotin, 1-carnitine, corticosterone, ethanolamine, d(+)-galactose, glutathione (reduced), linolenic acid, linoleic acid, retinyl acetate, selenium, T3 (triodo-1-thyronine), dl-α-tocopherol, dl-α-tocopherol acetate, catalase, and superoxide dismutase. In an embodiment, proteins and enzymes of the medium are isolated from human or are recombinant with a human sequence.

A composition is provided for differentiating stem cells into a differentiated cell of interest, the composition comprising isolated conditioned medium obtained from a culture of hepatoblasts cultured in a medium comprising a basal medium. Basal media are widely-known in the art, and as used herein are understood to encompass cell-growth media (for example, un-supplemented) used for culturing mammalian cells.

A composition is provided comprising isolated conditioned medium obtained from a culture of hepatoblasts cultured in a medium comprising a basal medium, or a basal medium further comprising two or more of phenacetin, phytosphingosine HCl, and pyridoxal HCl.

A composition is provided for differentiating stem cells into a differentiated cell of interest, the composition comprising conditioned medium obtained from a culture of hepatoblasts cultured in a medium comprising a basal medium, or a basal medium further comprising two or more of phenacetin, phytosphingosine HCl, and pyridoxal HCl. In an embodiment, (i) the medium comprising a basal medium from which the conditioned medium is obtained, or (ii) the basal medium further comprising two or more of phenacetin, phytosphingosine HCl, and pyridoxal HCl, also further comprises L-glutamine, non essential amino acids, and an antibiotic.

In an embodiment of the compositions, the medium comprising a basal medium further comprises L-glutamine, non essential amino acids, and an antibiotic. In an embodiment, the basal medium is a DMEM. In an embodiment, the antibiotic is penicillin-streptomycin. In an embodiment, the non-essential amino acids are glycine, L-alanine, L-asparagine, L-aspartic acid, L-glutamic acid, L-proline and L-serine. In an embodiment, the medium comprising a basal medium further comprises an artificial serum replacement.

In an embodiment of the compositions, the medium further comprises one or more of L-cysteinglutathione disulfide, γ-Glu-Cys, DL-kynurenine, D-penicillamine disulfide, and tetracaine HCl. In an embodiment, the medium does not comprise tetracaine HCl. In an embodiment, the medium comprises L-cysteinglutathione disulfide, γ-Glu-Cys, DL-kynurenine, D-penicillamine disulfide, phenacetin, phytosphingosine HCl, and pyridoxal HCl. In an embodiment, the aforelisted components are, independently, present at a concentration of 10 µM or less, of 7.5 µM or less, 5 µM or less, of 2.5 µM or less, or 1 µM or less. In an embodiment, the aforelisted components are, independently, present at a concentration of greater than 0.01 µM.

In an embodiment of the compositions, the medium comprises retinoic acid and/or dexamethasone. In an embodiment, the medium comprises L-glutamine. In an embodiment, the medium comprises a selenium compound. In an embodiment, the medium comprises sodium selenite. In an embodiment, the medium comprising a selenium compound also comprises one or more of an albumin, transferrin, insulin, progesterone, putrescine, biotin, 1-carnitine, corticosterone, ethanolamine, d(+)-galactose, glutathione (reduced), linolenic acid, linoleic acid, retinyl acetate, selenium, T3 (triodo-1-thyronine), dl-α-tocopherol, dl-α-tocopherol acetate, catalase, and superoxide dismutase. In an embodiment, proteins and enzymes of the medium are isolated from human or are recombinant with a human sequence.

In an embodiment of the compositions, the hepatoblasts are immortalized. In an embodiment, the hepatoblasts are human hepatoblasts. In an embodiment, the hepatoblasts are fetal hepatoblasts. In an embodiment, the hepatoblasts are immortalized human fetal hepatoblasts. In an embodiment, the hepatoblasts are mammalian, but are not human. In an embodiment, the hepatoblasts are human, but are not fetal.

In the various media described herein and in the various compositions comprising media, the specified components are present in amounts consistent with the health and/or growth of the cells in the medium.

A hepatocyte is an epithelial parenchymatous cell of the liver. In an embodiment, the hepatocyte is capable of secreting bile. In an embodiment, the hepatocyte is polygonal. Induced pluripotent stem cells are adult cells, typically somatic cells, that have been genetically reprogrammed to an embryonic stem cell-like state by being caused to express genes and factors important for maintaining the defining properties of embryonic stem cells. In an embodiment, the induced pluripotent stem cells are mammalian. In an embodiment, the adult cell from which the induced pluripotent stem cell is induced is a human adult cell. Embryonic stem cells are pluripotent stem cells derived from the inner cell mass of the blastocyst. In an embodiment, the embryonic stem cells are mammalian. In a further embodiment, the embryonic stem cells are non-human. In an embodiment, the embryonic stem cells are human. Basal media are serum-free media widely available in the art.

A method is provided for treating a liver disorder in a subject comprising administering to the subject an amount of the described compositions, or an amount of the described differentiated cells obtained by any of the methods described hereinabove, in an amount effective to treat a liver disorder.

A liver disorder is a disorder or pathology of the mammalian liver which impairs the proper functioning of the liver as compared to a healthy liver. Such disorders are widely known in the art.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Here, the principle is established that soluble signals from fetal liver cells undergoing hepatic development and with stem or progenitor cell properties can drive differentiation in pluripotent stem cells to generate hepatocytes in the meso-endodermal stage of fetal liver development. These pluripotent stem cell-derived hepatocytes expressed repertoires of hepatobiliary and mesenchymal genes, distinct microRNA profiles, as well as synthetic and metabolic hepatic functions, e.g., albumin secretion, urea production, and xenobiotic disposal, which recapitulated properties of fetal hepatocytes. Therefore, these hESC-derived cells were designated "embryonic/fetal hepatocyte-like cells" (eFHLC). It was found that hepatic functions were expressed at sufficient levels in eFHLC to sustain mice with fatal drug-induced acute liver failure (ALF) (11). In this setting, transplanted eFHLC provided liver support to prolong life. Moreover, eFHLC released paracrine factors that were capable of protecting hepatocytes in vitro and this mechanism promoted liver regeneration in vivo to complete rescue of mice with drug-induced ALF. Therefore, this method to manipulate pluripotent stem cells to generate hepatocytes in defined developmental stage and with appropriate hepatic potency offers opportunities for a variety of cell type-specific basic, clinical and other applications.

EXPERIMENTAL RESULTS

Example 1

Differentiation of pluripotent hESC generated hepatocytes: First, it was determined in what ways would soluble signals from immature fetal hepatocytes (FH) direct differentiation of hESC. To avoid donor-to-donor variability, FH immortalized by telomerase were used, with stem/progenitor cell properties, as well as meso-endodermal phenotype of primary FH (12-13). Conditioned medium (CM) was harvested from FH over 24 h and excluded serum. Feeder cells or animal additives were not included. A multi-step protocol was developed that included culture of hESC in FH-CM alone for first 3 d followed over the next 3 d by culture of hESC with FH-CM plus three known soluble factors and then further culture of hESC for a total of 14 d with FH-CM plus another known soluble factor. None of the soluble factors added to FH-CM was essential for initiating hepatic differentiation in hESC. However, in the presence of these known soluble factors, hESC adhered better in plastic culture dishes.

Figures 1A, 1B, 1C, 1D, 1E, 1F, 1G, 1H:
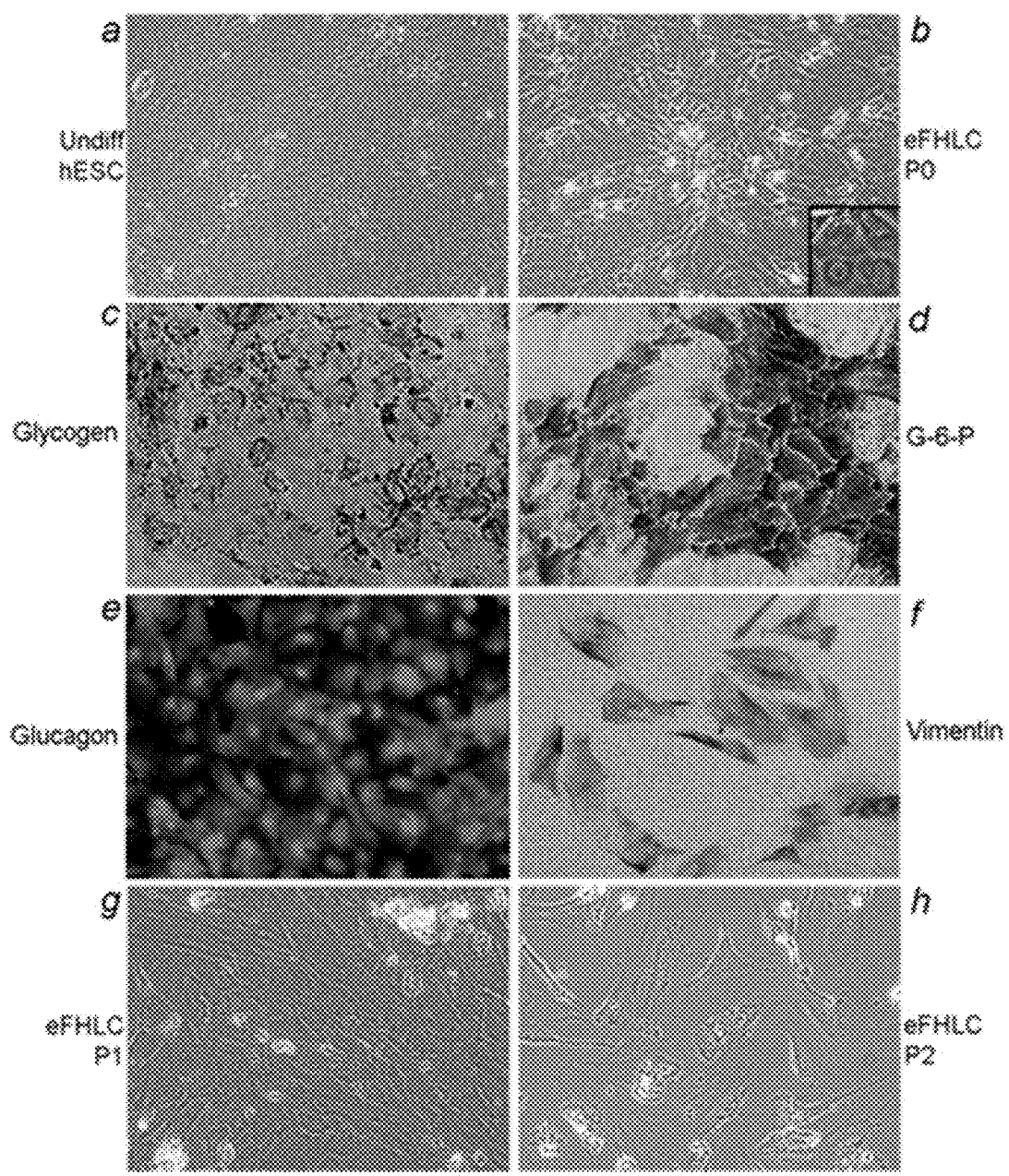
FIG. 1A-1H. Morphology of hESC cultured with FH-CM. (A) Undifferentiated hESC with clusters of small cells. (B) Primary embryonic/fetal hepatocyte-like cells (eFHLC) (P0) after 14 d with fetal hepatocyte-conditioned medium (FH-CM). Note larger cell size and epithelial morphology. Inset, higher magnification showing binucleation, common to hepatocytes. (C-F) eFHLC with glycogen, G6P, glucagon and vimentin. (G-H) eFHLC subpassaged once (P1) or twice (P2). Orig. Mag., ×200.
Figures 2A, 2B, 2C:
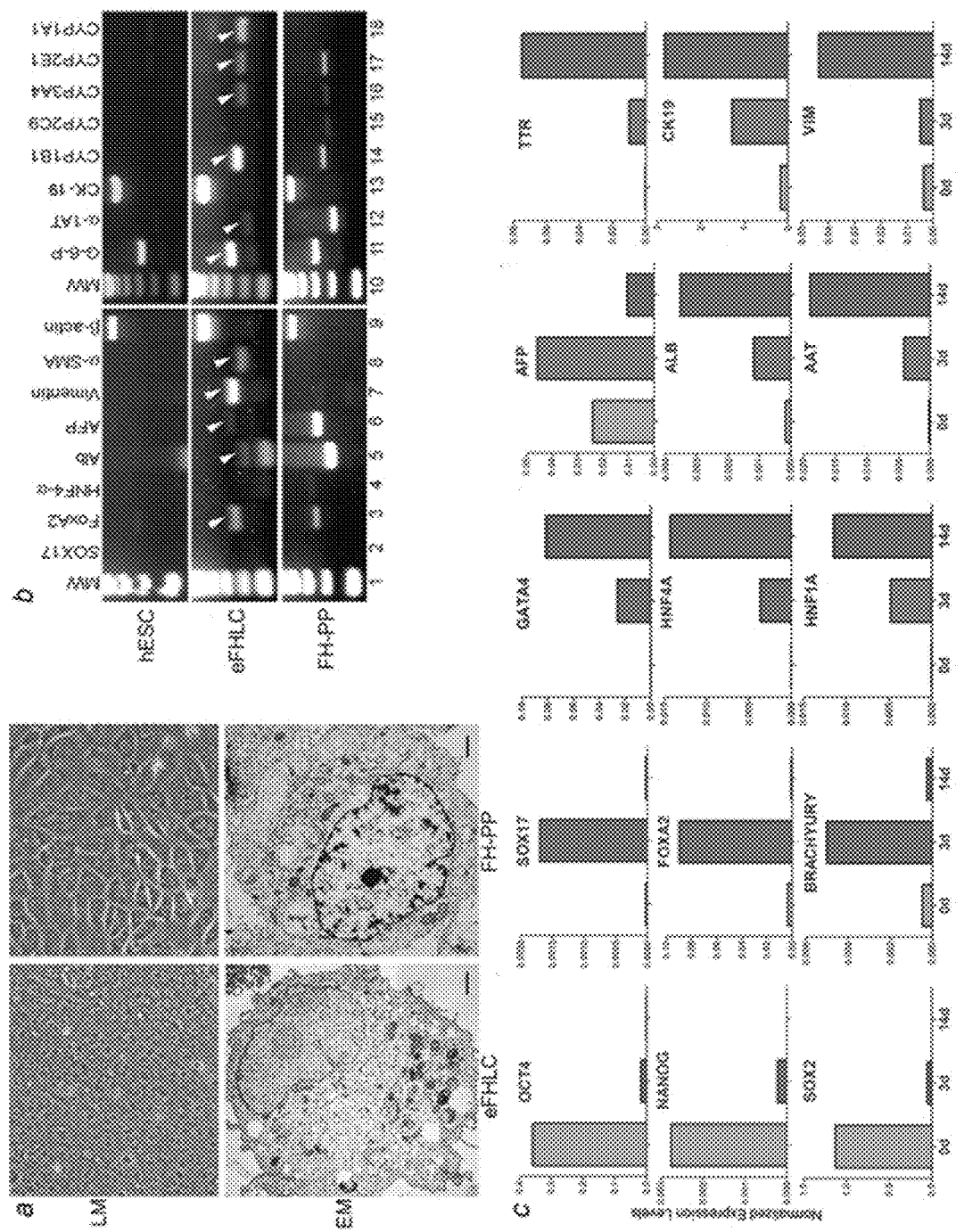
FIG. 2A-2C. Characterization of differentiating eFHLC. (A) Light and electron microscopy (LM, EM) in eFHLC and fetal human hepatocytes showing similarities in epithelial properties (EM, bottom; magnification bar=1 µm). (B) RT-PCR for gene expression in hESC, d14 eFHLC and freshly isolated fetal human hepatocytes. Arrowheads indicate endodermal and mesodermal markers in eFHLC. (C) Temporal gene expression profile by qRT-PCR in eFHLC over d0, d3 and d14. Pluripotency markers, OCT4, NANOG and SOX2 declined, endodermal markers, SOX17, FOXA2, and mesodermal marker, brachyrury, increased transiently, while hepatic transcription factors, GATA4, HNF4, HNF1A, were increasingly expressed. Hepatic genes, i.e., AFP, ALB, AAT, TTR, were coordinately expressed, along with biliary marker, CK19, and mesenchymal markers. Cluster analysis of global gene expression in hESC, eFHLC, freshly isolated fetal human hepatocytes (FH-PP) or cultured fetal human hepatocytes (FH-P3), and adult human hepatocytes (AH), showed convergence of eFHLC most towards FH-P3.
Figures 3A, 3B, 3C:
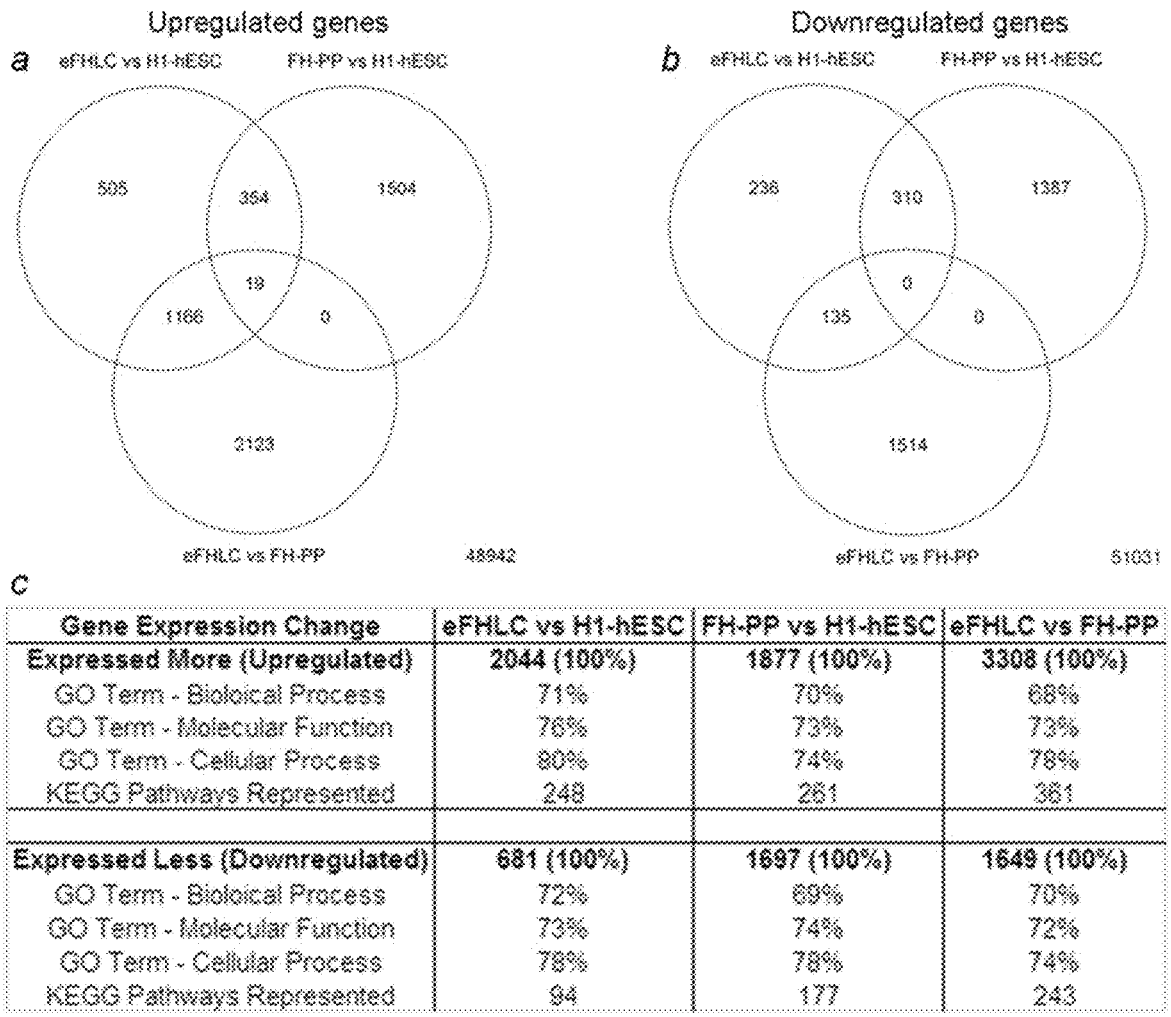
FIG. 3A-3C. Microarray analysis of gene expression in eFHLC versus hESC and freshly isolated fetal human hepatocytes (FH-PP). Panels A, B show global differences in gene expression. Data were from total gene sequences called as present, range, 48,942 to 51,031. In eFHLC, 505 or 2123 genes were uniquely upregulated versus hESC and FH-PP, respectively, and 236 or 1514 genes were uniquely downregulated versus hESC and FH-PP, respectively. By contrast, 1504 genes were uniquely upregulated and 1387 genes were uniquely downregulated in FH-PP cells versus hESC cells.

During differentiation, hESC in primary culture (P0) gained epithelial morphology within 3 d (FIG. 1A-1B). The eFHLC expressed liver/pancreas foregut endoderm markers, i.e., glycogen, glucose-6-phosphatase (G6P), glucagon, and others, and the mesenchymal marker, vimentin (VIM) (FIG. 1C-F). Over 14 d, $0.50\pm0.07\times10^6$ hESC originated $1.94\pm0.05\times10^6$ eFHLC, which constituted a 4-fold gain in cell numbers. Moreover, population doublings of eFHLC during P1 and P2 cultures (FIG. 1G-1H), produced >20-fold gains in their cell numbers, which indicated the ability of differentiating cells to continue proliferating, and was consistent with highly efficient generation of differentiated cells from pluripotent stem cells.

eFHLC were characterized by morphology, gene expression and functional assays. eFHLC acquired more cytoplasm, larger nuclei, even binucleated cells, similar to hepatocytes (FIG. 2A). Cytoplasmic complexity with lysosomes, microperoxisomes and vacuoles, resembled that in hepatocytes. Reverse transcription-polymerase chain reactions (RT-PCR) showed hepatic markers, i.e., α-fetoprotein (AFP), albumin (ALB), G6P, α-1-antitrypsin (AAT), cytokeratin (CK)-18, metabolic enzymes, e.g., CYP-1B1, -3A4, -2E1, and -1A1, and also mesenchymal markers, i.e., VIM, α-smooth muscle actin (aSMA) (FIG. 2B), confirming conjoint meso-endodermal phenotype of natural fetal hepatocytes (6,7). Temporal differentiation profile by quantitative RT-PCR was informative, as within 3 d, pluripotency-associated genes, i.e., OCT4, NANOG and SOX2, were expressed less, and endoderm-associated genes, i.e., SOX17, FOXA2, and early mesoderm-associated gene, brachyury, were expressed more (FIG. 2C, Table 2). By 14 d of epithelial advancement, E-cadherin (ECAD), a marker of epithelial cells, was well-expressed, which was paralleled by the appearance after 3 d and increase after 14 d of hepatic transcription factors, GATA4, HNF1a and HNF4a. Hepatic gene expression changed correspondingly, since AFP appeared after 3 d, and ALB, AAT or TTR increased between 3 d and 14 d. Similarly, expression of CYP3A4 and CYP7A1, which characterize mature hepatocytes, increased during this period. Nonetheless, VIM and CK19 expression after 14 d assigned eFHLC to the fetal hepatic stage. Global gene expression profiling by Affymetrix microarrays in hESC, eFHLC, primary or cultured fetal hepatocytes, and adult hepatocytes, substantiated this possibility, since eFHLC diverged from undifferentiated hESC and converged more along fetal than adult hepatocytes (FIG. 2D). In eFHLC, gene expression ontology and regulation of cytokine signaling trended toward fetal hepatocytes (FIG. 3). Global microRNA (miRNA) profiling showed several similarities between eFHLC and fetal hepatocytes when array analysis of cellular miRNA in eFHLC versus hESC and freshly isolated fetal human hepatocytes (FH-PP) was performed.

TABLE 2 qRT-PCR analysis of gene expression - Gene expression was normalized with β-actin and represents fold-change versus undifferentiated hESC on d 0 of differentiation protocol:

| Gene analyzed | Undifferentiated H1-hESC d 0 | eFHLC 3 d | eFHLC 14 d |
|---|---|---|---|
| Pluripotency markers | | | |
| OCT4 | 1.0 | 0.1 | 0 |
| NANOG | 1.0 | 0.1 | 0 |
| SOX2 | 1.0 | 0.1 | 0 |
| Endodermal markers | | | |
| BRACHYURY | 1.0 | 10 | 0.6 |
| SOX17 | 1.0 | 56 | 1.0 |
| FOXA2 | 1.0 | 27 | 0.2 |
| Epithelial marker | | | |
| CDH1 | 1.0 | 1.5 | 2.6 |
| Mesenchymal marker | | | |
| VIM | 1.0 | 1 | 11 |
| Hepatic transcriptional factors | | | |
| GATA4 | 1.0 | 155 | 488 |
| HNF4A | 1.0 | 165 | 653 |
| HNF1A | 1.0 | 58 | 136 |
| Hepatic markers | | | |
| AFP | 1.0 | 2 | 0.4 |
| ALB | 1.0 | 7 | 21 |
| AAT | 1.0 | 18 | 82 |
| TAT | 1.0 | 20 | 25 |
| TTR | 1.0 | 37 | 273 |
| TDO2 | 1.0 | 20 | 29 |
| ASGPR1 | 1.0 | 1 | 1.6 |
| APOF | 1.0 | 7 | 9 |
| CYP3A4 | 1.0 | 67 | 66 |
| CYP7A1 | 1.0 | 12 | 14 |
| G6P | 1.0 | 40 | 68 |
| Biliary marker | | | |
| CK19 | 1.0 | 8 | 17 |

Figures 4A, 4B, 4C, 4D, 4E, 4F:
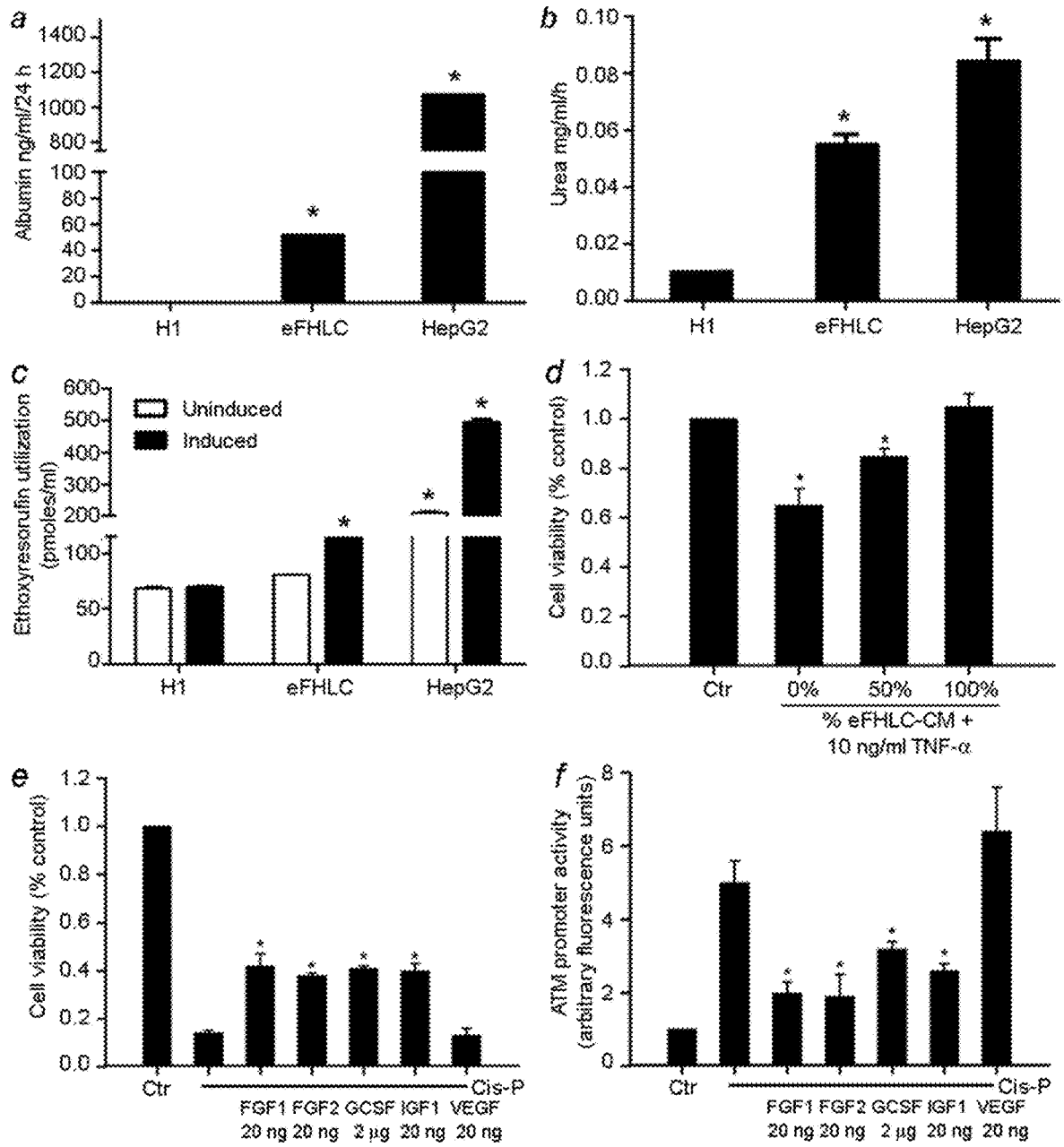
Figures 7A, 7B, 7C, 7D:
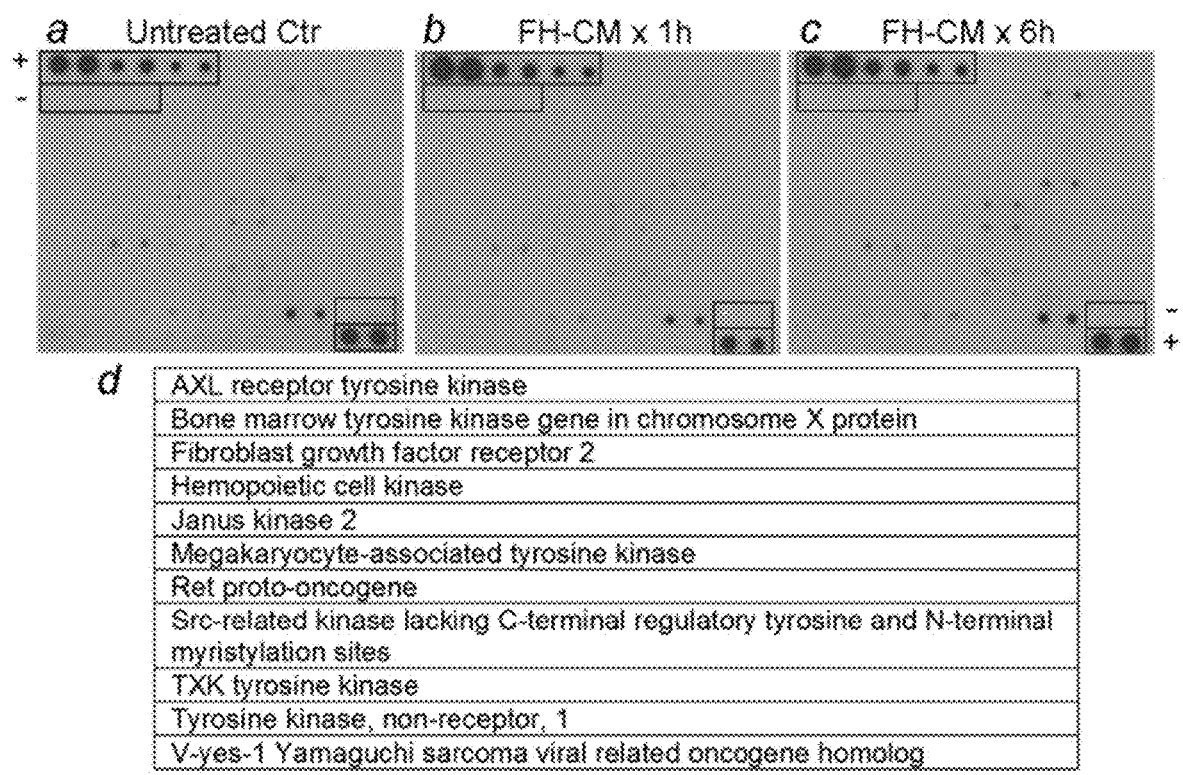

Protein studies verified mRNA findings in eFHLC as stem cell markers declined (OCT4, NANOG, TRA-1-80) and hepatic (FOXA2, ALB, G6P and glycogen) and biliary (GGT) properties increased. In d14 eFHLC, OCT4 was lost with gain of ECAD, VIM, FOXA2, and ALB expression. eFHLC contained hepatobiliary markers, glycogen, G6P and GGT. Similarly, epithelial (ECAD) and mesenchymal (VIM) markers were coexpressed. High level expression of asialoglycoprotein receptor (ASGPR1), which is specific to adult hepatocytes, indicated many eFHLC were maturing along the hepatic lineage. Flow cytometry showed 27% eFHLC expressed ASGPR1, marking mature hepatocytes.

eFHLC expressed hepatic synthetic, metabolic and xenobiotic disposal functions in vitro: After 14 d of differentiation, eFHLC secreted albumin, synthesized urea and converted a xenobiotic, ethoxyresorufin, to resorufin (FIG. 4A-4C). Such functions are important for hepatic support in liver failure (7, 11). Similarly, paracrine factors may protect hepatocytes from injury (14). This was confirmed since CM from eFHLC protected mouse hepatocytes from tumor necrosis factor (TNF)-α toxicity (FIG. 4D). Recently, it was established that drug-induced ALF in mice involved impairment in ataxia telangiectasia mutated (ATM) signaling (11), which is regulated by paracrine signals. Therefore, to demonstrate whether soluble factors could restore ATM signaling, lentivirally-modified Huh-7 cells were prepared (from human hepatocellular carcinoma) to express the tdTomato reporter gene under control of cloned human ATM promoter (15). When these hATMP-tdT cells were cultured with cis-platinum (Cis-P), DNA strand breaks were induced, cell viability declined and ATM promoter activity increased (FIG. 4E, 4F). It was found that culture of hATMP-tdT cells with Cis-P, plus FGF1, FGF2, G-CSF and IGF1 but not VEGF, improved cell viability and lowered ATM promoter activity. These factors had been identified to be present in eFHLC-CM (FIG. 5), which indicated that eFHLC were capable of affecting intracellular signaling through paracrine mechanisms.

eFHLC rescued mice with drug-induced ALF: Identification of hepatic functions and potential for paracrine signaling suggested eFHLC could support recovery of the damaged liver. This was facilitated by a NOD/SCID mouse model of ALF (11), where rifampicin (Rif), phenytoin (Phen) and monocrotaline (MCT) caused dysregulation of Atm signaling, leading to severe oxidative stress, DNA damage, hepatic necrosis, liver test abnormalities, coagulopathy, encephalopathy, and 90-100% mortality. Intraperitoneal transplantation of mature hepatocytes with microcarrier scaffolds rescued mice with ALF. Of note, transplanted hepatocytes remained in peritoneal cavity without migrating to the liver. Moreover, reseeding of the liver with cells was unnecessary. ALF was induced with Rif-Phen-MCT in mice (n=20), followed by 4-6×10⁶ eFHLC (n=10) or vehicle (n=10) i.p. In the FHLC group, 5 mice survived (50%) versus only 1 mouse in the vehicle group (10%), p<0.001. In eFHLC-treated mice, encephalopathy was absent or less severe, whereas sham-treated mice developed severe encephalopathy (grade 3-4), p<0.05. Liver tests improved in the eFHLC group versus the vehicle group. After 7 d, serum alanine aminotransferase (ALT) was 77±82 versus 4800±500 u/l and total bilirubin 0.5±0.2 versus 2.5±0.5 mg/dl, p<0.05. Normal blood glucose and serum creatinine levels in all mice excluded hypoglycemia or renal failure as coincidental causes of death. Human cells were identified in cell-microcarrier conglomerates recovered from peritoneal cavity. Histological sections of microcarrier (mc) and cell-conglomerates recovered from mice 7 d after eFHLC transplantation showed vascular reorganization (H&E staining), glycogen in transplanted cells, and confirmation of human transplanted cells by in situ hybridization for primate-specific centromere sequences. Transplanted eFHLC were absent from the native liver, as was expected. Livers of vehicle-treated mice were edematous, hemorrhagic and necrotic with extensive expression of phosphorylated histone H2AX, confirming oxidative DNA damage, and only interspersed Ki-67+ cells, indicating limited liver regeneration. In eFHLC-treated mice, liver necrosis and H2AX expression decreased, while the prevalence of Ki-67+ cells increased. Histological grading showed 5.4-fold less liver injury in eFHLC-treated mice after 7 d, 0.7±0.3 versus 3.8±0.4, p<0.05. The prevalence of Ki-67+ cells at that time was 2.3-fold greater in eFHLC-treated mice, 91±5 versus 39±4 cells/HPF, p<0.05. Analysis of hepatic gene expression indicated extensive perturbations in animals with ALF (Table 3). In eFHLC-treated mice, expression of genes in oxidative/metabolic stress, inflammatory cytokines, chemokines or other mediators, and of Atm and cell cycle regulators, i.e., Ccnc, Ccnd1 or Egr1, improved.

After i.p. or subcutaneous transplantation, eFHLC did not proliferate, and no tumors were observed in NOD/SCID mice over 3 months. Undifferentiated hESC generated teratomas as expected (not shown) (5-7).

TABLE 3

Liver mRNA expression by qRT-PCR (fold NOD/SCID mice versus mice in ALF with sham-treatment or of eFHLC transplantation - Data were first normalized against housekeeping β-actin gene in individual samples. Each condition was analyzed with samples in triplicate

| Gene description | Gene Symbol | Sham-3 d | Sham-7 d | eFHLC-3 d | eFHLC-7 d |
|---|---|---|---|---|---|
| Oxidative or Metabolic Stress | | | | | |
| Crystallite, alpha B | Cryab | −1.2 | 1.6 | 1.1 | −1.1 |
| Cytochrome P450, family 1, subfamily a, polypeptide 1 | Cyp1a1 | −3.7 | −4.9 | −5.8 | −4.7 |
| Cytochrome P450, family 1, subfamily b, polypeptide 1 | Cyp1b1 | −3.4 | 1.5 | −2.6 | −1.3 |
| Cytochrome P450, family 2, subfamily a, polypeptide 5 | Cyp2a5 | −6.7 | −5.1 | −1.1 | −1.9 |
| Cytochrome P450, family 2, subfamily b, polypeptide 10 | Cyp2b10 | −1.2 | 1.1 | −1.7 | −1.8 |
| Cytochrome P450, family 2, subfamily b, polypeptide 9 | Cyp2b9 | −7.3 | −7.2 | −7.3 | −2.1 |
| Cytochrome P450, family 2, subfamily c, polypeptide 29 | Cyp2c29 | −46.3 | −106.9 | −1.4 | −1.4 |
| Cytochrome P450, family 3, subfamily a, polypeptide 11 | Cyp3a11 | −13.8 | −27.7 | −9.1 | −4.8 |
| Cytochrome P450, family 4, subfamily a, polypeptide 10 | Cyp4a10 | 1.6 | −5.9 | −13.9 | −11.0 |
| Cytochrome P450, family 4, subfamily a, polypeptide 14 | Cyp4a14 | 7.8 | −2.0 | −7.8 | −18.8 |
| Cytochrome P450, family 7, subfamily a, polypeptide 1 | Cyp7a1 | −32.9 | −100.2 | −64.1 | −11.7 |
| Epoxide hydrolase 2, cytoplasmic | Ephx2 | −4.1 | −10.4 | −2.6 | −2.0 |
| Flavin containing monooxygenase 1 | Fmo1 | −15.6 | −2.3 | −1.9 | −1.3 |
| Flavin containing monooxygenase 4 | Fmo4 | −1.2 | −2.0 | −2.1 | −2.2 |
| Flavin containing monooxygenase 5 | Fmo5 | 1.7 | −1.3 | 1.0 | −1.6 |
| Glutathione peroxidase 1 | Gpx1 | −3.2 | −3.1 | −3.0 | −2.1 |
| Glutathione peroxidase 2 | Gpx2 | −1.6 | −1.1 | −1.7 | 1.0 |
| Glutathione reductase | Gsr | −1.4 | −1.4 | −2.1 | −2.0 |
| Glutathione S-transferase, mu 1 | Gstm1 | −3.8 | −10.6 | −5.8 | −2.5 |
| Glutathione S-transferase, mu 3 | Gstm3 | −3.9 | −5.8 | −1.1 | 1.8 |
| Heme oxygenase (decycling) 1 | Hmox1 | 1.1 | 3.5 | 2.2 | −1.1 |
| Heme oxygenase (decycling) 2 | Hmox2 | −1.2 | −1.6 | −2.4 | −3.0 |
| Metallothionein 2 | Mt2 | 5.7 | 7.8 | 17.8 | −2.1 |
| Polymerase (RNA) II (DNA directed) polypeptide K | Polr2k | −1.5 | −1.2 | −2.7 | −2.3 |
| P450 (cytochrome) oxidoreductase | Por | −1.7 | −5.9 | −2.5 | −4.4 |
| Superoxide dismutase 1, soluble | Sod1 | −2.7 | −3.6 | −7.5 | −6.0 |
| Superoxide dismutase 2, mitochondrial | Sod2 | −4.4 | −5.4 | 1.3 | −1.1 |
| Heat Shock | | | | | |
| DnaJ (Hsp40) homolog, subfamily A, member 1 | Dnaja1 | −1.9 | −2.8 | −3.9 | −3.4 |
| Heat shock factor 1 | Hsf1 | −1.4 | −1.7 | −1.8 | −1.7 |
| Heat shock protein 1B | Hspa1b | −1.9 | −1.1 | −1.5 | −2.0 |
| Heat shock protein 1-like | Hspa1l | −2.8 | −4.0 | −7.4 | −3.7 |
| Heat shock protein 4 | Hspa4 | −1.5 | −3.3 | −1.7 | 1.0 |
| Heat shock protein 5 | Hspa5 | 1.9 | 1.5 | −1.1 | −1.4 |
| Heat shock protein 8 | Hspa8 | −1.0 | −1.2 | −1.4 | −1.4 |
| Heat shock protein 1 | Hspb1 | −1.2 | 1.8 | −1.7 | −2.0 |
| Heat shock protein 1 (chaperonin) | Hspd1 | −1.6 | −2.4 | −1.7 | −1.7 |
| Heat shock protein 1 (chaperonin 10) | Hspe1 | −1.7 | −1.7 | −2.4 | −2.3 |
| Proliferation and Carcinogenesis | | | | | |
| Colony stimulating factor 2 (granulocyte-macrophage) | Csf2 | −1.2 | 2.6 | −1.4 | 1.1 |
| Cyclin C | Ccnc | −1.7 | −1.7 | 3.6 | 4.2 |
| Cyclin D1 | Ccnd1 | −1.1 | 1.8 | 6.7 | 12.9 |
| Cyclin G1 | Ccng1 | 1.4 | 2.4 | 1.2 | 1.9 |
| E2F transcription factor 1 | E2f1 | −1.0 | 2.2 | 1.4 | 2.2 |
| Early growth response 1 | Egr1 | 4.2 | 15.3 | 30.6 | 9.7 |
| Proliferating cell nuclear antigen | Pcna | −1.3 | 1.4 | −1.0 | −1.0 |
| Growth Arrest and Senescence | | | | | |
| Cyclin-dependent kinase inhibitor 1A (P21) | Cdkn1a | 105.0 | 92.0 | 141.4 | 116.5 |
| DNA-damage inducible transcript 3 | Ddit3 | 1.2 | 3.9 | 2.1 | 1.1 |
| Growth arrest and DNA-damage-inducible 45 alpha | Gadd45a | −3.1 | 1.6 | −2.1 | −5.7 |
| Insulin-like growth factor binding protein 6 | Igfbp6 | −10.2 | −3.5 | −101.8 | −110.4 |
| Transformed mouse 3T3 cell double minute 2 | Mdm2 | −1.0 | 1.8 | 5.4 | 4.7 |
| Transformation related protein 53 | Trp53 | −1.3 | 1.3 | −1.1 | −1.1 |
| Inflammation | | | | | |
| Chemokine (C-C motif) ligand 21b | Ccl21b | −5.0 | −16.6 | −16.1 | −16.6 |
| Chemokine (C-C motif) ligand 3 | Ccl3 | 5.4 | 30.7 | 6.3 | 4.4 |
| Chemokine (C-C motif) ligand 4 | Ccl4 | 3.4 | 21.5 | 8.1 | 3.7 |
| Chemokine (C-X-C motif) ligand 10 | Cxcl10 | 2.4 | 10.8 | 4.5 | 1.1 |
| Interleukin 18 | Il18 | −3.0 | −2.1 | −3.6 | −2.9 |
| Interleukin 1 alpha | Il1a | −2.9 | 1.0 | −1.3 | −1.2 |
| Interleukin 1 beta | Il1b | 1.2 | 3.5 | 1.6 | 1.4 |
| Interleukin 6 | Il6 | 1.9 | 7.3 | 6.0 | 1.8 |
| Lymphotoxin A | Lta | −1.2 | 1.1 | — | −1.8 |
| Macrophage migration inhibitory factor | Mif | −1.5 | −1.3 | 1.9 | 1.3 |
| Nuclear factor of kappa light polypeptide gene enhancer in B-cells 1, p105 | Nfkb1 | −1.3 | 1.5 | −1.3 | −1.5 |

TABLE 3-continued

Liver mRNA expression by qRT-PCR (fold NOD/SCID mice versus mice in ALF with sham-treatment or of eFHLC transplantation - Data were first normalized against housekeeping β-actin gene in individual samples. Each condition was analyzed with samples in triplicate

| Gene description | Gene Symbol | Sham-3 d | Sham-7 d | eFHLC-3 d | eFHLC-7 d |
|---|---|---|---|---|---|
| Nitric oxide synthase 2, inducible | Nos2 | 6.5 | 24.4 | 26.5 | 1.8 |
| Serine (or cysteine) peptidase inhibitor, clade E, member 1 | Serpine1 | 50.8 | 57.3 | 286.0 | 7.4 |
| DNA Damage and Repair | | | | | |
| Ataxia telangiectasia mutated homolog (human) | Atm | −1.7 | −2.4 | −1.3 | 1.1 |
| CHK2 checkpoint homolog (S. pombe) | Chek2 | −1.1 | 1.6 | −1.2 | −1.1 |
| Excision repair cross-complementing rodent repair deficiency, complementation group 1 | Ercc1 | 1.1 | 2.1 | 1.2 | −1.1 |
| Excision repair cross-complementing rodent repair deficiency, complementation group 4 | Ercc4 | −1.5 | −2.0 | −2.4 | −2.1 |
| RAD23a homolog (S. cerevisiae) | Rad23a | −2.0 | −2.7 | −3.0 | −2.8 |
| RAD50 homolog (S. cerevisiae) | Rad50 | −1.8 | −1.5 | 1.3 | 1.3 |
| UDP glucuronosyltransferase 1 family, polypeptide A2 | Ugt1a2 | −2.8 | −3.1 | −3.2 | −2.5 |
| Uracil DNA glycosylase | Ung | −1.7 | −1.4 | 1.9 | −1.4 |
| X-ray repair complementing defective repair in Chinese hamster cells 1 | Xrcc1 | −1.3 | −1.4 | −2.8 | −2.4 |
| X-ray repair complementing defective repair in Chinese hamster cells 2 | Xrcc2 | 1.4 | 1.1 | 1.7 | 1.4 |
| X-ray repair complementing defective repair in Chinese hamster cells 4 | Xrcc4 | −1.1 | −1.0 | −1.4 | −1.6 |
| Apoptosis Signaling | | | | | |
| Annexin A5 | Anxa5 | 2.9 | 5.0 | 4.4 | 2.4 |
| Bcl2-associated X protein | Bax | 1.5 | 2.3 | 1.2 | 1.2 |
| Bcl2-like 1 | Bcl2l1 | 1.7 | 2.6 | 3.9 | 1.9 |
| Caspase 1 | Casp1 | −2.4 | 1.7 | −1.5 | −1.2 |
| Caspase 8 | Casp8 | −4.3 | −1.1 | −1.1 | 1.1 |
| Fas ligand (TNF superfamily, member 6) | Fasl | −1.2 | 1.2 | −1.7 | −1.8 |
| Nuclear factor of kappa light polypeptide gene enhancer in B-cells inhibitor, alpha | Nfkbia | −1.3 | 1.7 | −1.1 | −1.4 |
| Tumor necrosis factor receptor superfamily, member 1a | Tnfrsf1a | 1.1 | 1.5 | 1.7 | 1.1 |
| Tumor necrosis factor (ligand) superfamily, member 10 | Tnfsf10 | −4.3 | −3.4 | −6.3 | −4.9 |
| TNFRSF1A-associated via death domain | Tradd | −1.6 | −1.3 | −2.3 | −1.9 |

Mechanisms in hepatic differentiation of hESC: To understand how FH-CM caused hepatic differentiation in hESC, cytokines and growth factors were examined, and 62 of 507 such proteins were found to be present in FH-CM (FIG. 6), including regulators of cell differentiation, e.g., activinA, FGFs, or transforming growth factors (TGF) (12, 13). As signal transduction through these molecules should have engaged receptors on cell surface followed by phosphorylation of receptor tyrosine kinases (RTKs), 71 RTKs were examined in hESC stimulated with FH-CM for 10 min, 1 h or 6 h. Surprisingly, RTKs were not activated, including receptors of 12 ligands present in FH-CM (FIG. 7). To determine whether proteins in FH-CM were dispensable for hESC differentiation, FH-CM was degraded by heating to 100° C., and passed FH-CM through Amicon membranes to remove >3 kilodalton size proteins. Protein-depleted FH-CM still induced epithelial differentiation in hESC, including changes in morphology and gene expression, including in expression of pluripotency (Nanog, Sox-2), epithelial (AFP), or mesenchymal (VIM) genes within 3 d (FIG. 8). It was concluded that nonprotein molecules in FH-CM were involved. These molecules were stable since FH-CM generated eFHLC despite storage of FH-CM for 6 weeks at 4° C. To characterize the nature of nonprotein components in FH-CM, the Purdue University Metabolite Profiling Facility performed LC-MS metabolomics analysis, which identified 810 compounds with good separations in blank medium and FH-CM. Of these 810 compounds, 105 compounds were >3-fold abundant in FH-CM versus blank medium, p<0.03 (Table 4).

Genes expressed under differentiation conditions were analyzed by qRT-PCR with customized array from SA Biosciences. Expression of individual genes was normalized against housekeeping gene, β-actin. The data indicated culture of hESC with protein-depleted FH-CM was effective in initiating differentiation along meso-endodermal hepatic stage. Most notable were decreases in expression of Nanog and Sox2 and increases in expression of AFP and VIM.

TABLE 1

Changes in gene expression. (C) Genes expressed under differentiation conditions. Gene expression was analyzed by qRT-PCR with customized array from SA Biosciences.

| | Undifferentiated H1-hESC | FH-CM-treated eFHLC x 3 d | |
|---|---|---|---|
| Gene analyzed | | Heat-denatured | 3 kd Amicon cut-off |
| Pluripotency genes | | | |
| OCT4 | 1.0 | 1.3 | 1.3 |
| NANOG | 1.0 | 0.3 | 0.1 |
| SOX2 | 1.0 | 0.7 | 0.3 |
| Endoderm markers | | | |
| BRACHYURY | 1.0 | 0.5 | 1.9 |
| SOX17 | 1.0 | 0.7 | 1.0 |
| FOXA2 | 1.0 | 0.3 | 1.2 |
| Epithelial marker | | | |
| CDH1 | 1.0 | 0.7 | 0.9 |

TABLE 1-continued

Changes in gene expression. (C) Genes expressed under differentiation conditions. Gene expression was analyzed by qRT-PCR with customized array from SA Biosciences.

| Gene analyzed | Undifferentiated H1-hESC | FH-CM-treated eFHLC x 3 d | |
|---|---|---|---|
| | | Heat-denatured | 3 kd Amicon cut-off |
| Mesenchymal marker | | | |
| VIM | 1.0 | 6.2 | 4.6 |
| Hepatic transcription factors | | | |
| GATA4 | 1.0 | 0.5 | 1.5 |
| HNF4A | 1.0 | 1.0 | 2.0 |
| HNF1A | 1.0 | 0.4 | 1.4 |
| Hepatic markers | | | |
| AFP | 1.0 | 1.3 | 2.5 |
| ALB | 1.0 | 0.7 | 2.0 |
| AAT | 1.0 | 0.5 | 1.8 |
| TAT | 1.0 | 0.6 | 1.9 |
| TTR | 1.0 | 0.5 | 1.7 |
| TDO2 | 1.0 | 0.6 | 1.7 |
| ASGPR1 | 1.0 | 0.9 | 1.5 |
| APOF | 1.0 | 0.5 | 1.9 |
| CYP3A4 | 1.0 | 0.6 | 1.4 |
| CYP7A1 | 1.0 | 0.7 | 3.3 |
| G6P | 1.0 | 0.5 | 2.0 |
| Biliary marker | | | |
| CK19 | 1.0 | 0.7 | 0.6 |

TABLE 4

Listing of compounds identified by LC-MS metabolomics analysis in FH-CM

| Compound, Exact Mass | Retention Time (min) | Corrected p-value | Compound Identification |
|---|---|---|---|
| 281.1072 | 1.93 | 1.37E−09 | 281.1072 |
| 448.0098 | 2.00 | 1.22E−09 | 448.0098 |
| 426.0855 | 2.02 | 2.94E−10 | Cysteineglutathione disulfide |
| 197.0828 | 2.15 | 3.49E−12 | N-benzylideneaniline n-oxide |
| 374.1351 | 2.17 | 6.77E−13 | 374.1351 |
| 380.1687 | 2.25 | 5.35E−09 | Asn Thr Phe |
| 211.0454 | 2.25 | 1.13E−09 | 211.0454 |
| 156.0031 | 2.50 | 2.26E−11 | C6 H7 N P S |
| 128.0112 | 2.51 | 1.08E−13 | 128.0112 |
| 268.0192 | 2.53 | 3.57E−13 | 268.0192 |
| 161.0683 | 2.54 | 1.55E−05 | 2-Aminoadipic acid |
| 226.9919 | 2.64 | 1.92E−10 | 226.9919 |
| 1092.4396 | 2.65 | 1.06E−10 | 1092.4396 |
| 339.0923 | 2.66 | 1.17E−12 | Cys Ser Met |
| 380.1361 | 2.67 | 7.25E−04 | C15 H29 N2 O3 P S2 |
| 408.1783 | 2.67 | 2.01E−05 | Tryptophan |
| 373.1532 | 2.71 | 2.22E−12 | C15 H20 N9 O P |
| 135.0547 | 2.71 | 1.44E−14 | Adenine |
| 301.1136 | 2.84 | 7.53E−10 | C9 H15 N7 O5 |
| 210.9971 | 2.85 | 3.14E−09 | 210.9971 |
| 380.1367 | 2.90 | 1.01E−10 | C15 H29 N2 O3 P S2 + 2.9005 |
| 90.0319 | 2.96 | 2.24E−16 | Lactic acid |
| 323.0060 | 3.00 | 4.68E−13 | C24 H4 P |
| 167.0584 | 3.08 | 7.45E−14 | Pyridoxal (Vitamin B6) |
| 250.0623 | 3.47 | 3.36E−11 | gamma-L-Glutamyl-L-cysteine |
| 122.0487 | 3.90 | 1.71E−09 | Niacinamide |
| 201.1666 | 4.04 | 2.92E−12 | C12 H25 S |
| 149.0510 | 4.05 | 3.76E−10 | Methionine |
| 268.0713 | 4.72 | 9.69E−05 | Homolanthionine |
| 444.1428 | 4.75 | 1.39E−08 | 444.1428 |

TABLE 4-continued

Listing of compounds identified by LC-MS metabolomics analysis in FH-CM

| Compound, Exact Mass | Retention Time (min) | Corrected p-value | Compound Identification |
|---|---|---|---|
| 396.0489 | 5.00 | 4.58E−12 | C21 H8 N4 O5 |
| 329.9910 | 5.07 | 3.49E−12 | C19 H9 P3 |
| 214.0085 | 5.09 | 4.95E−12 | 2,3-Dioxogulonic acid |
| 296.0869 | 5.35 | 9.46E−15 | Penicillamine disulfide |
| 233.1224 | 6.30 | 3.27E−09 | C11 H23 O P2 |
| 401.1190 | 9.24 | 1.77E−07 | C17 H25 N2 O5 S2 |
| 612.1535 | 11.45 | 4.66E−10 | Glutathione, oxidized |
| 208.0851 | 12.83 | 8.30E−13 | Kynurenine |
| 159.0685 | 15.31 | 2.39E−15 | Indoleacetaldehyde |
| 266.0351 | 32.20 | 1.27E−08 | C13 H15 P S2 |
| 482.1143 | 34.69 | 6.19E−13 | C16 H26 N4 O9 S2 |
| 383.1070 | 35.60 | 2.47E−15 | Succinoadenosine |
| 135.0558 | 35.62 | 1.08E−13 | C7 H7 N2 O |
| 297.0898 | 35.63 | 4.09E−15 | 5'-Methylthioadenosine |
| 313.0839 | 35.63 | 2.22E−13 | C13 H12 N7 O P |
| 369.4807 | 36.70 | 2.74E−10 | 369.4807 |
| 315.2040 | 36.76 | 4.82E−12 | C15 H23 N8 |
| 499.1462 | 37.07 | 9.72E−11 | C23 H28 N5 O2 P3 |
| 249.5732 | 37.30 | 7.64E−10 | 249.5732 |
| 595.1771 | 37.42 | 2.15E−11 | 8-Hydroxy-perphenazine glucuronide |
| 1482.8310 | 37.65 | 1.69E−09 | 1482.831 |
| 556.1732 | 37.71 | 3.76E−12 | C23 H28 N9 O4 P2 |
| 639.1682 | 38.11 | 3.28E−13 | 639.1682 |
| 179.0950 | 38.20 | 2.24E−16 | Phenacetine |
| 264.1823 | 38.21 | 3.28E−12 | Tetracaine |
| 312.1465 | 38.38 | 3.54E−13 | Phe Phe |
| 514.1626 | 38.43 | 2.11E−10 | C21 H26 N9 O3 P2 |
| 252.0902 | 38.49 | 5.52E−11 | Carbamazepine 10,11-epoxide |
| 485.0762 | 38.74 | 5.00E−06 | C27 H19 N O4 S2 |
| 1471.5754 | 38.79 | 3.76E−10 | 1471.5754 |
| 450.8249 | 38.79 | 6.24E−11 | 450.8249 |
| 1024.2646 | 38.80 | 5.22E−10 | 1024.2646 |
| 374.1240 | 38.81 | 1.14E−11 | C27 H19 P |
| 771.3008 | 38.83 | 7.29E−12 | 771.3008 |
| 916.2433 | 38.89 | 2.75E−09 | FMNH |
| 346.0992 | 38.95 | 7.64E−10 | C25 H14 O2 |
| 582.1468 | 38.99 | 3.49E−12 | C27 H25 N10 P3 |
| 590.1166 | 38.99 | 6.94E−12 | 5-Aminoimidazole ribonucleotide |
| 574.1458 | 39.10 | 1.39E−08 | C28 H26 N6 O4 S2 |
| 450.8238 | 39.32 | 1.38E−10 | 450.8238 |
| 578.2068 | 39.32 | 3.49E−12 | C36 H37 O P3 |
| 265.0948 | 39.45 | 6.24E−11 | 265.0948 |
| 262.0776 | 39.54 | 1.57E−06 | C8 H16 N5 O S2 |
| 574.1232 | 39.67 | 4.57E−13 | C24 H34 N O7 P2 S2 |
| 558.1804 | 39.74 | 6.47E−07 | C35 H30 N2 O S2 |
| 276.0570 | 39.83 | 3.89E−13 | C15 H9 N4 P |
| 421.1670 | 39.83 | 1.87E−06 | C13 H27 N9 O3 S2 |
| 208.5870 | 39.92 | 4.39E−09 | 208.587 |
| 574.1265 | 40.06 | 3.42E−11 | C28 H31 O7 P S2 |
| 558.1820 | 40.24 | 1.31E−06 | C23 H34 N4 O8 S2 |
| 447.1469 | 40.38 | 1.58E−10 | C23 H30 N O2 P S2 |
| 622.1914 | 40.39 | 2.50E−10 | 622.1914 |
| 314.1083 | 40.70 | 3.28E−13 | C21 H17 N P |
| 558.1816 | 40.84 | 1.35E−07 | C23 H34 N4 O8 S2 + 40.837997 |
| 290.1090 | 40.97 | 3.66E−11 | C15 H18 N2 O2 S |
| 350.0953 | 41.14 | 6.53E−10 | N-acetylaspartate |
| 330.1974 | 41.31 | 9.31E−14 | C16 H30 N2 O3 S |
| 507.1460 | 41.32 | 2.60E−11 | C32 H29 P2 S |
| 290.1086 | 41.42 | 2.29E−11 | C15 H18 N2 O2 S + 41.415 |
| 706.1547 | 41.52 | 6.64E−11 | 706.1547 |
| 324.1161 | 41.76 | 2.29E−10 | acetohexamide |
| 1170.3890 | 41.81 | 4.73E−12 | 1170.389 |
| 507.1476 | 42.27 | 2.81E−10 | C30 H24 N2 O4 P |
| 324.1154 | 42.45 | 4.93E−12 | C19 H19 N O2 P |
| 317.2929 | 42.65 | 9.15E−12 | Phytosphingosine |

TABLE 4-continued

Listing of compounds identified by LC-MS metabolomics analysis in FH-CM

| Compound, Exact Mass | Retention Time (min) | Corrected p-value | Compound Identification |
|---|---|---|---|
| 507.1482 | 43.29 | 2.20E−12 | 1-deoxy-1-[methyl[3-phenyl-3-[4-(trifluoro-methyl)phenoxy]pro-pyl]amino]-b-D-Glucopyranuronic acid |
| 382.1235 | 43.56 | 4.58E−12 | C20 H22 N3 O P2 |
| 366.1256 | 43.63 | 6.18E−05 | C17 H22 N2 O5 S |
| 906.3010 | 44.60 | 3.26E−10 | 906.301 |
| 583.0971 | 45.71 | 4.27E−09 | 583.0971 |
| 354.2546 | 46.00 | 3.63E−12 | 5beta-Chola-3,8(14),11-trien-24-oic Acid |
| 541.1893 | 46.15 | 6.05E−08 | C29 H33 O8 S |
| 234.1606 | 46.18 | 2.09E−10 | 3-n-decyl acrylic acid |
| 517.3172 | 47.16 | 4.12E−11 | Linolenoyl lysolecithin |
| 541.3209 | 47.22 | 4.31E−10 | 541.3209 |

Discussion

Direct differentiation of hESC with FH-CM rapidly and efficiently generated hepatocytes, leading to uniformity of hepatic development, including expression of hepatic transcription factors, coordinately-regulated hepatobiliary genes, epithelial markers, as well as mesenchymal markers. This recapitulated the meso-endodermal stage of natural fetal hepatocytes (4-7). The extent of synthetic, metabolic and xenobiotic disposal functions further confirmed this developmental stage in eFHLC. Despite this immaturity, transplanted eFHLC rescued mice in ALF by providing critical life-support and paracrine signals to aid liver repair/regeneration, which was similar to the capability in this setting of mature hepatocytes (7, 11).

Previously, lack of knowledge or uncertainties in the hepatic lineage stage achieved made it difficult to interpret the efficacy of stem cell differentiation protocols (1-3, 18-21). Use of FH-CM without animal-derived materials, feeder cells or genetic manipulation to express multiple transcription factors avoided previous major restrictions (22). These attributes should be especially helpful for developing further insights into liver cell differentiation mechanisms in stem cells, as well as various applications of stem cell-derived liver cells.

FH-CM induced hepatic differentiation in hESC by the steps of endoderm specification followed by maturation to fetal stage. This reproduced paracrine effects of proteins during differentiation of mouse stem cells in vitro (17). However, hepatic differentiation induced by FH-CM lacking proteins was singularly different from cell differentiation induced by cytokine/chemokine/growth factor-based protocols. Despite the presence in FH-CM of proteins affecting cell attachment and perhaps proliferation, e.g., activinA, FGFs, GCSF, interleukin-6, TNF, VEGF, etc., (14, 18, 23, 24), deficiency of RTK activation in hESC substantiated that these proteins did not play seminal roles in stem cell differentiation with FH-CM. The findings indicated active role in stem cell differentiation of natural small compounds in FH-CM. Whether these compounds could additionally have emanated from eFHLC themselves during cell differentiation was unknown. Previously, screening of chemical libraries identified synthetic candidate compounds advancing β islet cell differentiation (25). These results are different from the present findings because small molecules in FH-CM originated naturally from cells. Among the list of these small compounds, putative differentiation-inducing molecules included those affecting differentiation in stem/progenitor cells, e.g., 2-aminoadipic acid (26). Use of specific matrices and synthetic surfaces could help in further expanding eFHLC or other stem cell-derived cell types.

Protein secretion, urea synthesis and xenobiotic metabolism in eFHLC indicated suitable hepatic properties. Cells engrafted and functioned in xenotolerant mice, which was similar to mature human hepatocytes (27). After transplantation, stem cell-derived hepatocytes may engraft and express liver functions in animals, although often largely at mRNA level (5-7, 22, 28) On the other hand, for cell therapy requiring organ repopulation with healthy cells, proliferation of transplanted cells is critical (22, 28). In treating genetic conditions permanently, extensively modified cells, e.g., those reprogrammed with multiple transcription factors, will be less desirable than cells differentiated simply by extracellular soluble signals. It should be noteworthy that in settings, such as ALF, where short-term liver support by extrahepatic reservoirs of cells rescued animals without need for reseeding of the liver with cells, other considerations are applicable (7, 11). For instance, eFHLC showed capacity for glucose homeostasis, protein synthesis and ammonia detoxification, besides releasing hepatoprotective substances, e.g., FGFs, GCSF, IGFs, VEGF, etc. Previously, only GCSF was known to regulate ATM promoter activity (29). It was found that FGFs and IGF also regulated hepatic ATM signaling. As molecular perturbations, including ATM signaling, improved after eFHLC transplantation, this added specificity to the effects of cell therapy in ALF.

Materials and Methods

Studies were approved according to NIH guidelines, by the Einstein Committee on Clinical Investigations, Embryonic Stem Cell Research Oversight Committee, and Animal Care and Use Committee.

Fetal cells: Fetal livers were from Human Fetal Tissue Repository at Einstein. Ep-CAM+ liver cells were isolated and cultured as previously described (5, 6). hTERT-FH-B cells were cultured in DMEM with 10% FBS (12). To obtain CM, hTERT-FH-B were cultured for 24 h in DMEM/F12 medium with 2% Knock-out Serum Replacer (KSR), 2 mM L-glutamine, 0.1 mM MEM Non Essential Amino Acids (NEAA), 1% penicillin-streptomycin (Invitrogen Corp., Carlsbad, CA).

Culture of hESC. WA-01 hESC were passaged weekly on matrigel-coated dishes in DMEM/F12 medium, 1% B27 supplement, 1% N2 supplement, 2 mM L-glutamine, 0.1 mM NEAA, 1% penicillin-streptomycin (Invitrogen Corp.) and 50 ng/ml basic FGF (R&D Systems, Minneapolis, MN). For the final hepatic differentiation protocol, hESC were washed with DMEM/F12, and cultured in FH-CM.

Cytotoxicity assays. For effects of CM from hFHLC on TNF-α-induced cytotoxicity, $1.5 \times 10^5$ primary mouse hepatocytes were isolated by collagenase perfusion (11), and plated in 24-well dishes in RPMI 1640 medium with 10% FBS and antibiotics. After overnight culture, cells were switched to CM plus 10 ng/ml TNF-α (Sigma) for 16-18 h, followed by thiazolyl blue viability assays, as described previously (14). For cisP toxicity assays, Huh-7 cells were used after transduction by a lentiviral vector to express human ATM promoter-driven tdTomato gene (15). Huh-7 cells cultured with 15 μM cis-P (Sigma) or 2 μg/ml G-CSF (Amgen Inc., Thousand Oaks, CA) for 16-18 h were incubated for 20 min with 6 μg/ml Hoechst33342 (Sigma) for cell viability and TdTomato/ATM promoter expression.

Hepatic functions. For albumin, cell culture medium harvested after 3 h was analyzed by human albumin immunoassay (Bethyl Laboratories, Montgomery, TX). For ureagenesis, cells were incubated with 2.5-7.5 mM ammonium chloride for 12 h and urea content was analyzed as previously described (27). For CYP450 activity, cells were induced overnight with phenobarbital, 7-ethoxyresorufin and μM dicumarol were added for 12 h at 37° C., and resorufin was measured, as described previously (30).

Human cytokine arrays. Conditioned medium was analyzed by human antibody array I membrane for 507 human proteins and cell lysates were analyzed by Human RTK Phosphorylation Antibody Array 1 (RayBiotech, Norcross, GA), according to manufacturer.

NOD/SCID mice with ALF. CB17.NOD/SCID$^{prkdc}$ mice, 6-7 weeks old, were from Jackson Labs. (Bar Harbor, ME). Mice were given 3 daily doses of i.p. Rif (75 mg/kg) and Phen (30 mg/kg) followed by one i.p. dose on d4 of MCT (160 mg/kg), as described previously.[11] After 1 d, 4-6×10$^6$ hESC-derived cells differentiated for 14 d were transplanted i.p. with 1 ml Cytodex 3™ microcarriers (Amersham Biosciences Corp., Piscataway, NJ). Sham-treated animals received microcarriers. Encephalopathy was graded from 0 (absent) to 3 (coma). Mice were observed for 2 weeks. In some studies, hESC-derived cells were injected subcutaneously or i.p. for tumor formation over 3 months.

Immunohistochemistry. Cells were fixed in 4% paraformaldehyde in phosphate buffered saline, pH 7.4 (PBS), blocked/permeabilized with 5% goat serum, 0.2% Triton X-100 (Sigma) in PBS for 1 h, and incubated overnight at 4° C. with anti-human antibodies for OCT3/4 (1:200), AFP (1:100), ECAD (1:50) (Santa Cruz Biotechnology Inc., Santa Cruz, CA), FOXA2 (1:100) (R&D Systems), ALB (1:200) (Sigma), VIM (1:100) (US Biologicals, Swampscott, MA). After washing in PBS, TRITC-conjugated goat anti-mouse IgG (1:50, Sigma) or anti-rabbit IgG (1:100) were added for 1 h with 4'-6-diamidino-2-phenylindole (DAPI) (Invitrogen) counterstaining. In negative controls, primary antibodies were omitted. Glycogen, G-6-P, and GGT were stained as described (4-7).

Electron microscopy. Cells were fixed in 2.5% glutaraldehyde in cacodylate butter, postfixed in osmium tetroxide, and stained with 1% uranyl acetate before embedding in plastic. Ultrathin sections were examined under JEOL 1200 electron microscope.

Molecular studies. RNA was extracted by TRIzol reagent (Invitrogen), cleaned by RNeasy (Qiagen Sciences, Germantown, MD), incubated in DNase I (Invitrogen) and reverse-transcribed by Omniscript RT kit (Qiagen). Platinum PCR SuperMix (Invitrogen) was used for PCR with annealing at 94° C.×5 min, and 35 cycles at 94° C.×30 s, 55° C.×30 s, 72° C.×45 s, and 72° C.×10 min (primers, Table 4). Mouse Stress and Toxicity RT$^2$ Profiler PCR Array and RT$^2$ Real-Time SyBR Green PCR mix and RT$^2$ First Strand kit were from SABiosciences (Frederick, MD). cDNA synthesis and PCR was according to the manufacturer. For quantitative (q) RT-PCR analysis of gene expression, customized arrays were obtained for 24 genes, including pluripotency genes, transcription factors and hepatobiliary genes (CAPH-0800A; SA Biosciences). Data were analyzed by 2-ΔΔCt method. Fold-changes in gene expression were expressed as log-normalized ratios from sham-treated/normal and cell transplantation/normal livers. Gene expression was analyzed with U133 2.0 Plus oligonucleotide arrays (Affymetrix Corp., Santa Clara, CA) as described (10). Changes in mRNA expression were examined for pathway-specificity by IPA tools (Ingenuity Systems Inc., Redwood, CA).

TABLE 5

Primer sequences for RT-PCR (SEQ ID NOS. 1-24, top to bottom, respectively).

| Gene | Primer sequence 5'-3' | Amplicon size expected |
|---|---|---|
| OCT4 | F: GACAACAATGAAAATCTTCAGGAGA<br>R: TTCTGGCGCCGGTTACAGAACCA | 218 bp |
| ALB | F: TGCTTGAATGTGCTGATGACAGGG<br>R: AAGGCAAGTCAGCAGGCATCTCATC | 161 bp |
| AFP | F: TGCAGCCAAAGTGAAGAGGGAAGA<br>R: CATAGCGAGCAGCCCAAAGAAGAA | 260 bp |
| CK-19 | F: ATGGCCGAGCAGAACCGGAA<br>R: CCATGAGCCGCTGGTACTCC | 308 bp |
| VIM | F: CACCTACAGCCTCTACG<br>R: AGCGGTCATTCAGCTC | 170 bp |
| α-SMA | F: AGTACCCGATAGAACATGG<br>R: TTTTCTCCCGGTTGGC | 153 bp |
| CYP1B1 | F: CACCAAGGCTGAGACAGTGA<br>R: GCCAGGTAAACTCCAAGCAC | 230 bp |
| CYP2C9 | F: GGACAGAGACGACAAGCACA<br>R: TGGTGGGGAGAAGGTCAAT | 200 bp |
| CYP3A4 | F: TGTGCCTGAGAACACCAGAG<br>R: GCAGAGGAGCCAAATCTACC | 201 bp |
| CYP2E1 | F: CCGCAAGCATTTTGACTACA<br>R: GCTCCTTCACCCTTTCAGAC | 202 bp |
| CYP1A1 | F: AGGCTTTTACATCCCCAAGG<br>R: GCAATGGTCTCACCGATACA | 197 bp |
| β-Actin | F: TCACCACCACGGCCGAGCG<br>R: TCTCCTTCTGCATCCTGTCG | 350 bp |

Abbreviations: F, Forward; R, Reverse; bp, base pair; ALB, albumin; AFP, α-fetoprotein; CK-19, cytokeratin-19; VIM, vimentin; SMA, smooth muscle actin, CYP, cytochrome P450

For microRNAs, total RNA isolated by TRIzol reagent (Invitrogen) was analyzed by LC Sciences (Houston, TX) with probe set based on Sanger miRBase, v 9.0. Later, transcripts with <500 arbitrary signals were excluded as these are not identified by qRT-PCR. Data were transformed to log 2 followed by clustering of transcripts (Cluster3, Stanford University) and heatmaps were drawn (JavaTree1.1.6r2).

Tissue studies: Tissue samples were frozen to −80° C. in methylbutane. Cryostat sections were prepared. Tissue morphology was analyzed by H&E stained sections. Tissue injury was graded as previously described (38). For hepatic function in transplanted cells, glycogen and G-6-P were stained (35). For Ki67 and histone H2AX, tissues were fixed in 4% PAF followed by rabbit anti-Ki67 (1:750, Vector Laboratories, Burlingame, CA) or rabbit anti-phosphoS139 H2AX (1:300, ab2893; Abcam, Cambridge, MA), respectively, and secondary anti-Rabbit Alexa Fluor 546 (1:500, Molecular Probes), followed by counterstaining with DAPI (7, 11). Transplanted cells were identified by in situ hybridization for alphoid satellite sequences in centromeres (27).

Liquid chromatography-mass spectroscopy (LC-MS) metabolomics. For non-targeted metabolite screen by LC-MS, 5 uL media were injected and separated on Agilent 1100 system with Waters Atlantis T3 column (3 μm, 150×2.1 mm i.d.). Binary mobile phase consisting of solvent systems A (0.1% formic acid in ddH$_2$O, v/v) and B (0.1% formic acid in acetonitrile, v/v) were used in gradient elution with flow of 0.3 mL/min. Initial conditions were set at 100:0 A:B, 1 min hold was employed followed by linear gradient to 70:30 at 20 min and linear gradient to 10:90 at 45 min. Gradient conditions were reset to 100:0 A:B from 45.1 min to 55 min. After separation, column effluent was introduced by positive mode electrospray ionization into Agilent MSD-TOF mass spectrometer. Mass data from m/z 70-1100 were collected. Biomarkers were identified with Agilent Mass Profiler Professional software, as recommended. These studies were performed by Bruce Cooper at Purdue University Metabolite Profiling Facility.

Serological studies. Sera were stored at −20° C. and analyzed for ALT and bilirubin as previously described. Human albumin was measured by immunoassay (Bethyl Laboratories).

Statistical analysis. Data were analyzed by t-tests, Pearson correlation tests, logrank tests, and ANOVA with Holm-Sidak posthoc test. P values <0.05 were considered significant.

Example 2

Differentiation of human embryonic stem cells (hESC) by synthetic counterparts of substances made naturally in fetal hepatocytes: The list of principal components identified by LC-MS in conditioned medium from fetal hepatocytes (FH-CM), which was provided in Table 4 was further reduced to a set of 8 compounds (CP) (commercially available in chemically synthesized form) (Table 6).

TABLE 6

CP tested for induction of hepatic differentiation in hESC and iPSC

| CP designation | Chemical identity | Exemplary Manufacturer | Catalog No. |
|---|---|---|---|
| 1 | L-Cysteinglutathione Disulfide | Santa Cruz | sc-211701 |
| 2 | γ-Glu-Cys | Sigma | G0903 |

TABLE 6-continued

CP tested for induction of hepatic differentiation in hESC and iPSC

| CP designation | Chemical identity | Exemplary Manufacturer | Catalog No. |
|---|---|---|---|
| 3 | DL-Kynurenine | Sigma | 61250 |
| 4 | D-Penicillamine disulfide | Sigma | P1101 |
| 5 | Phenacetin | Sigma | 77440 |
| 6 | Phytosphingosine HCl | Sigma | P2795 |
| 7 | Pyridoxal HCl | Sigma | P6155 |
| 8 | Tetracaine HCl | Sigma | T7508 |

The ability of these CP to substitute for FH-CM in differentiating hESC (WA-01 line) was examined in various combinations of CP (see Table 7) in micromolar concentrations of 1, 5, 10, 15, 20, and 25. Amounts of >10 micromolar of the compounds caused toxicity with cell death and detachment of hESC (WA-01 line) from surfaces of cell culture dishes. When these 8 CP were tested in hESC individually in medium (see methods), none of the CP in 1, 5 or 10 micromolar amounts induced hepatic differentiation, and OCT4 was still expressed, albumin or vimentin was not expressed, and cell morphology was unchanged. These 8 CP were then tested in concentrations of 5 or 10 micromolar each in combinations to substitute for FH-CM in differentiating hESC.

TABLE 7

Combinations of CP and their effects on induction of hepatic differentiation in hESC and iPSC¶

| Combination of compounds in culture (+, present; −, absent) | CP 1 | CP 2 | CP 3 | CP 4 | CP 5 | CP 6 | CP 7 | CP 8 | Hepatic differentiation induced? |
|---|---|---|---|---|---|---|---|---|---|
| 1 | + | − | − | − | − | − | − | − | No (only undifferentiated hESC) |
| 2 | + | + | − | − | − | − | − | − | No (only undifferentiated hESC) |
| 3 | + | + | + | − | − | − | − | − | No (only undifferentiated hESC) |
| 4 | + | + | + | + | − | − | − | − | No (only undifferentiated hESC) |
| 5 | + | + | + | + | + | − | − | − | Yes but incomplete (undifferentiated hESC present) |
| 6 | + | + | + | + | + | + | − | − | Yes but incomplete (undifferentiated hESC present) |
| 7 | + | + | + | + | + | + | + | − | Yes (most optimal with no obvious undifferentiated hESC) |
| 8 | + | + | + | + | + | + | + | + | Yes (but less optimal versus 7CP group of row above) |

¶Hepatic differentiation was evaluated by characteristic morphology of undifferentiated stem cells and of epithelial cells along with albumin staining.

Figures 9A, 9B, 9C, 9D, 9E, 9F:
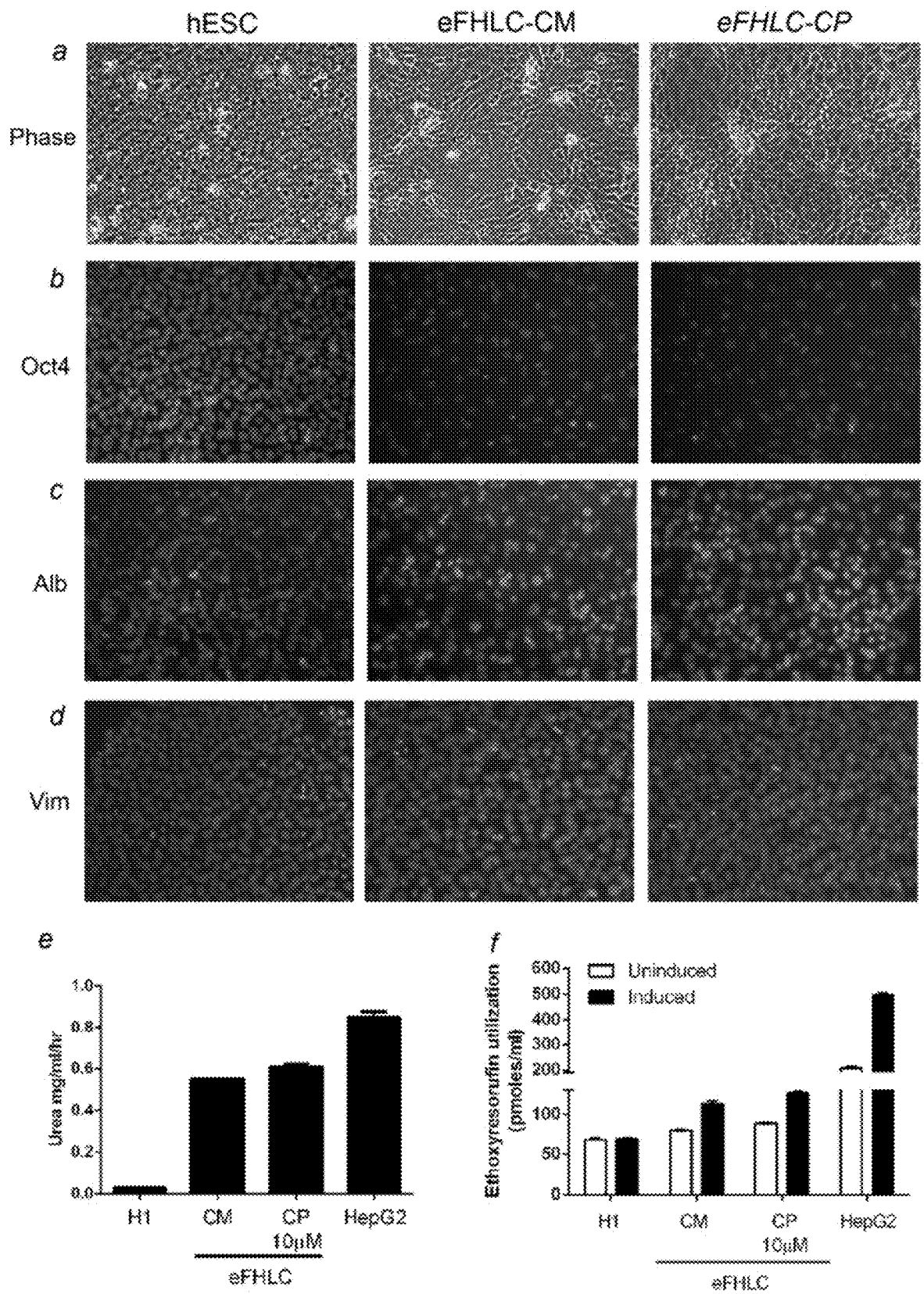

The culture medium contained additives, including retinoic acid, dexamethasone. Amounts of >10 micromolar of the compounds caused toxicity with cell death and detachment of adherent hESC from surfaces of cell culture dishes. Further analysis indicated culture of hESC with CP individually or in groupings of up to 6 CP at one time in 1, 5 or 10 micromolar amounts, did not alter morphology of cultured hESC and these continued to display characteristic small sizes and cluster formation (not shown). By contrast, culture of hESC with a group of 7 CP in 5 or 10 micromolar concentrations for 2 weeks generated large cells with uniform morphology of epithelial cells (FIG. 9A). The following combinations of CP were ineffective in hESC differentiation: CP1+CP2; CP1+CP2+CP3; CP1+CP2+CP3+CP4. The following combinations of CP were partially effective because both undifferentiated hESC and differentiated cells were present in culture dishes: CP5+CP6; CP6+CP7; and CP5+CP6+CP7. By contrast, when 7 or 8 CP were combined together, only differentiated cells were present in culture dishes. Of these two combinations, the following group of CP was most effective: CP1+CP2+CP3+CP4+CP5+CP6+CP7.

Figures 10A, 10B, 10C, 10D, 10E, 10F:
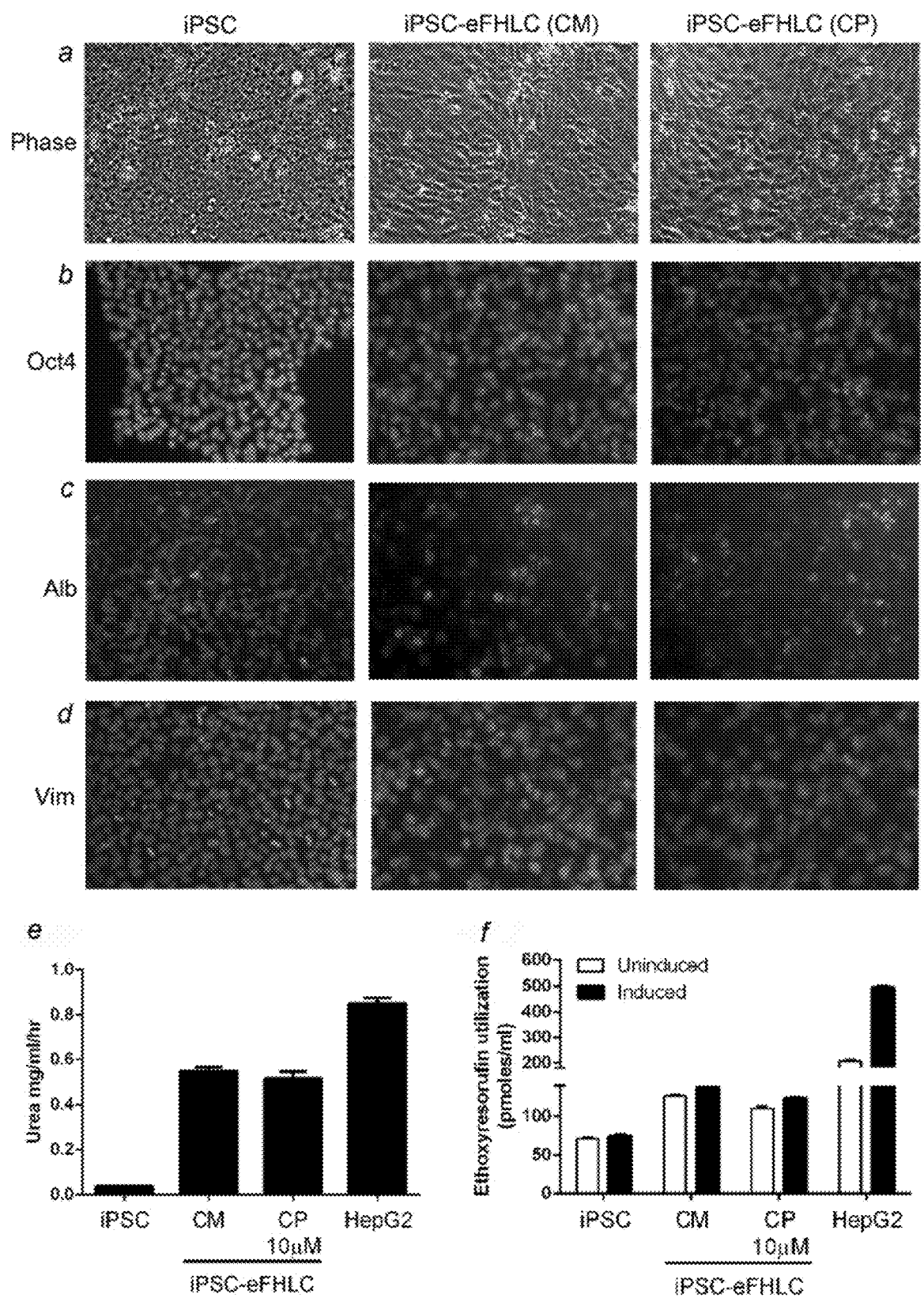

Further studies were performed of hESC-derived epithelial cells with this set of 7 CP. In response to the most effective combination of 7 CP, morphology of undifferentiated hESC changed and expression of OCT4 was no longer observed in differentiated hESC (FIG. 9A, 9B). Differentiated cells showed albumin in cytoplasm indicating hepatic differentiation, whereas undifferentiated hESC were negative for albumin staining (FIG. 9C). Moreover, differentiated cells expressed vimentin (FIG. 9D). The differentiated cells generated by 7 CP synthesized urea (FIG. 9E) and possessed ability to convert a xenobiotic, ethoxyresorufin, into resorufin (FIG. 9F). These properties were similar to hESC-derived cells generated by FH-CM (see Example 1).

iPSC were utilized that were obtained by reprogramming of normal human fibroblasts with non-integrating Sendai virus vectors from the Pluripotent Stem Cell Core at Albert Einstein College of Medicine. The differentiation protocol with FH-CM and CP was identical to studies with hESC described above. After 2 weeks, iPSC cultured with FH-CM became larger with epithelial morphology, whereas undifferentiated iPSC were smaller and were arranged in clusters (FIG. 10A). Similarly, iPSC cultured with above-described combination of 7 CP became larger with epithelial morphology. Expression of OCT4 was lost in iPSC cultured with either FH-CM or combination of 7 CP (FIG. 10B). Differentiated cells contained albumin as shown by immunostaining, whereas undifferentiated iPSC were negative for albumin staining (FIG. 10C). Moreover, similar to differentiation of hESC under these conditions, we found differentiated cells expressed vimentin. These iPSC-derived hepatocytes synthesized urea and metabolized ethoxyresorufin to resorufin (FIG. 10E, 10F). This substantiated that this combination of 7 CP generated hepatocytes from iPSC.

Materials and Methods

Chemicals and reagents: CP were purchased and stock solutions were prepared in either water or ethanol as recommended by the manufacturers (Sigma Chemical Co.; Santa Cruz Biotechnology).

Cells and cell culture: WA-01 hESC were passaged on matrigel-coated dishes in DMEM/F12 medium, 1% B27 supplement, 1% $N_2$ supplement, 2 mM L-glutamine, 0.1 mM NEAA (Life Technologies) and 50 ng/ml basic FGF (R&D Systems). The iPSC were generated from normal human fibroblasts with CytoTune®-iPS Sendai Reprogramming Kit (Life Technologies, Cat #A1378001). The iPSC were cultured on matrigel-coated dishes in DMEM/F12 medium, 1% B27 supplement, 1% $N_2$ supplement, 2 mM L-glutamine, 0.1 mM NEAA (Life Technologies) and 50 ng/ml basic FGF (R&D Systems). To obtain FH-CM, hTERT-FH-B cells were cultured for 24 h in DMEM/F12 medium with 2% Knock-out Serum Replacer (KSR), 2 mM L-glutamine, 0.1 mM MEM Non Essential Amino Acids (NEAA), 1% penicillin-streptomycin (Life Technologies).

Hepatic differentiation: For differentiation, hESC/iPSC were washed with DMEM/F12 and cultured for 2 weeks in FH-CM and CP in DMEM/F12 with 2% Knock-out Serum Replacer (KSR), 1% B27 supplement, 2 mM L-glutamine, 0.1 mM MEM Non-Essential Amino Acids (NEAA), 1% penicillin-streptomycin (Life Technologies). For testing effects of CP in differentiation of hESC/iPSC, identical culture medium was used except that one or more CP were added and the step of incubating hTERT-FH-B cells in this medium was omitted. HepG2 cells of human origin were included in some studies and were cultured in usual conditions with serum-containing medium as described in the parent document.

Immunostaining: Cells were fixed in 4% paraformaldehyde in phosphate buffered saline, pH 7.4 (PBS), blocked/permeabilized with 5% goat serum, 0.2% Triton X-100 (Sigma) in PBS for 1 h, and incubated overnight at 4° C. with mouse anti-human albumin antibody (HSA-11 clone, 1:200, Sigma), anti-human OCT3/4 (1:200, Santa Cruz Biotecnology), anti-human vimentin (1:100, US Biologicals). After washes in PBS, TRITC-conjugated goat anti-mouse IgG (1:50, Sigma) cells were counterstained for 1 h with 4'-6-diamidino-2-phenylindole (DAPI) (Life Technologies). In negative controls, primary antibody was omitted.

Hepatic functions: For ureagenesis, cells were incubated with 5 mM ammonium chloride for 12 h and analyzed as described (Cho et al., 2004, (31)). For CYP450 activity, cells were analyzed for 7-ethoxyresorufin conversion, as described (Gupta et al., 1999, (32)).

REFERENCES

1. Chinzei, R., et al. Embryoid-body cells derived from a mouse embryonic stem cell line show differentiation into functional hepatocytes. *Hepatology* 36, 22-29 (2002).
2. Karp, J. M., et al. Cultivation of human embryonic stem cells without the embryoid body step enhances osteogenesis in vitro. *Stem Cells* 24, 835-843 (2006).
3. Cai, J., et al. Directed differentiation of human embryonic stem cells into functional hepatic cells. *Hepatology* 45, 1229-1239 (2007).
4. Inada, M., et al. Stage-specific regulation of adhesion molecule expression segregates epithelial stem/progenitor cells in fetal and adult human livers. *Hepatol Int* 2, 50-62 (2008).
5. Malhi, H., Irani, A. N., Gagandeep, S. & Gupta, S. Isolation of human progenitor liver epithelial cells with extensive replication capacity and differentiation into mature hepatocytes. *J Cell Sci* 115, 2679-2688 (2002).
6. Inada, M., et al. Phenotype reversion in fetal human liver epithelial cells identifies the role of an intermediate meso-endodermal stage before hepatic maturation. *J Cell Sci* 121, 1002-1013 (2008).
7. Bandi, S., Joseph, B., Cheng, K. & Gupta, S. Spontaneous origin from human embryonic stem cells of early developmental stage liver cells displaying conjoint meso-endodermal phenotype with hepatic functions. *J Cell Sci* 2012; in press.
8. Moore, R. N. & Moghe, P. V. Expedited growth factor-mediated specification of human embryonic stem cells toward the hepatic lineage. *Stem Cell Res* 3, 51-62 (2009).
9. Johannesson, M., et al. FGF4 and retinoic acid direct differentiation of hESCs into PDX1-expressing foregut endoderm in a time- and concentration-dependent manner. *PLoS ONE* 4, e4794 (2009).
10. Ding, B. S., et al. Inductive angiocrine signals from sinusoidal endothelium are required for liver regeneration. *Nature* 468, 310-5 (2010).

11. Bandi, S., et al. Perturbations in Atm signaling pathways following drug-induced acute liver failure and their reversal during rescue of animals by cell therapy. *Am J Pathol* 178, 161-74 (2011).
12. Wege, H., et al. Telomerase reconstitution immortalizes human fetal hepatocytes without disrupting their differentiation potential. *Gastroenterology* 124, 432-444 (2003).
13. Zalzman, M. et al. Reversal of hyperglycemia in mice using human expandable insulin-producing cells differentiated from fetal liver progenitor cells. *Proc Natl Acad Sci USA* 100, 7253-8 (2003).
14. Enami, Y., et al. Hepatic stellate cells promote hepatocyte engraftment in rat liver after prostaglandin-endoperoxide synthase inhibition. *Gastroenterology* 136, 2356-64 (2009).
15. Shaner, N. C., et al. Improved monomeric red, orange and yellow fluorescent proteins derived from Discosoma sp. red fluorescent protein. *Nat Biotechnol* 22, 1567-72 (2004).
16. D'Amour, K. A., et al. Efficient differentiation of human embryonic stem cells to definitive endoderm. *Nat Biotechnol* 23, 1534-1541 (2005).
17. Soto-Gutierrez, A., et al. Differentiation of mouse embryonic stem cells to hepatocyte-like cells by co-culture with human liver nonparenchymal cell lines. *Nat Protoc* 2, 347-356 (2007).
18. Lavon, N., Yanuka, O. & Benvenisty, N. Differentiation and isolation of hepatic-like cells from human embryonic stem cells. Differentiation 72, 230-238 (2004).
19. Rambhatla, L., Chiu, C. P., Kundu, P., Peng, Y. & Carpenter, M. K. Generation of hepatocyte-like cells from human embryonic stem cells. Cell Transplant 12, 1-11 (2003).
20. Hay, D. C., et al. Highly efficient differentiation of hESCs to functional hepatic endoderm requires ActivinA and Wnt3a signaling. *Proc Natl Acad Sci USA* 105, 12301-12306 (2008).
21. Shiraki, N., et al. Differentiation of mouse and human embryonic stem cells into hepatic lineages. *Genes Cells* 13, 731-746 (2008).
22. Huang, P., et al. Induction of functional hepatocyte-like cells from mouse fibroblasts by defined factors. *Nature* 475, 386-9 (2011).
23. Jung, J., Zheng, M., Goldfarb, M. & Zaret, K. S. Initiation of mammalian liver development from endoderm by fibroblast growth factors. *Science* 284, 1998-2003 (1999).
24. Piscaglia, A. C., Shupe, T. D., Oh, S. H., Gasbarrini, A. & Petersen, B. E. Granulocyte-colony stimulating factor promotes liver repair and induces oval cell migration and proliferation in rats. *Gastroenterology* 133, 619-31 (2007).
25. Chen, S., et al. A small molecule that directs differentiation of human ESCs into the pancreatic lineage. *Nat Chem Biol* 5, 258-65 (2009).
26. Takeda, M., et al. Alpha-aminoadipate induces progenitor cell properties of Müller glia in adult mice. *Invest Ophthalmol Vis Sci* 49, 1142-50 (2008).
27. Cho, J. J., et al. Analysis of the functional integrity of cryopreserved human liver cells including xenografting in immunodeficient mice to address suitability for clinical applications. *Liver Int* 24, 361-370 (2004).
28. Basma, H., et al. Differentiation and transplantation of human embryonic stem cell-derived hepatocytes. *Gastroenterology* 136, 990-999 (2009).
29. Gueven, N., et al. Site-directed mutagenesis of the ATM promoter: consequences for response to proliferation and ionizing radiation. *Genes Chromosomes Cancer* 38, 157-167 (2003).
30. Gupta, S., et al. Position-specific gene expression in the liver lobule is directed by the microenvironment and not by the previous cell differentiation state. *J Biol Chem* 274, 2157-2165 (1999).
31. Cho, J. J., Joseph, B., Sappal, B. S., Giri, R. K., Wang, R., Ludlow, J. W., Furth, M. E., Susick, R., and Gupta, S. (2004). Analysis of the functional integrity of cryopreserved human liver cells including xenografting in immunodeficient mice to address suitability for clinical applications. Liver Int 24, 361-370.
32. Gupta, S., Rajvanshi, P., Sokhi, R. P., Vaidya, S., Irani, A. N., and Gorla, G. R. (1999). Position-specific gene expression in the liver lobule is directed by the microenvironment and not by the previous cell differentiation state. J Biol Chem 274, 2157-2165.

---

What is claimed:

1. A method of producing differentiated cells with hepatocyte-like function comprising culturing pluripotent stem cells in a cell culture medium comprising:
L-cysteinglutathione disulfide,
γ-Glu-Cys,
DL-kynurenine,
D-penicillamine disulfide,
phenacetin,
phytosphingosine HCl,
pyridoxal HCl,
and optionally, an additional antibiotic;
wherein the differentiated cells are characterized by:
(a) decreased Octamer-binding transcription factor 4 (OCT4) expression relative to undifferentiated stem cells;
(b) increased vimentin expression relative to the undifferentiated stem cells;
(c) increased synthesis of albumin relative to the undifferentiated stem cells;
(d) increased synthesis of urea relative to the undifferentiated stem cells;
(e) epithelial morphology relative to the undifferentiated stem cells;
(f) increased metabolism of ethoxyresorufin into resorufin relative to the undifferentiated stem cells; and
(g) increased cytochrome P450 activity relative to the undifferentiated stem cells.

2. The method of claim 1, wherein the additional antibiotic is tetracaine HCl.

3. The method of claim 1, wherein the cell culture medium does not contain the additional antibiotic.

4. The method of claim 1, wherein culturing the pluripotent stem cells in the cell culture medium is for a period of from 1 hour to 2 weeks.

5. The method of claim 1, further comprising wherein culturing the pluripotent stem cells in the cell culture medium is for a period of from 24 hours to 2 weeks.

6. The method of claim 1, further comprising wherein culturing the pluripotent stem cells in the cell culture medium is for a period of 2 weeks.

7. The method of claim 1, wherein the differentiated cells are produced from human embryonic stem cells (hESC).

8. The method of claim 1, wherein the differentiated cells are prepared from induced pluripotent stem cells (iPSC).

9. The method of claim 1, wherein culturing the pluripotent stem cells is in DMEM/F12 medium.

10. The method of claim 9, wherein the DMEM/F12 medium further comprises 2% Knock-out Serum Replacer (KSR), 1% B27 supplement, 2 mM L-glutamine, 0.1 mM MEM Non-Essential Amino Acids (NEAA), and 1% penicillin-streptomycin.

11. The method of claim 1, wherein the cell culture medium substantially omits conditioned medium from fetal hepatocytes (FH-CM).

12. The method of claim 1, wherein the concentration of each of L-cysteinglutathione disulfide, γ-Glu-Cys, DL-kynurenine, D-penicillamine disulfide, phenacetin, phytosphingosine HCl, and pyridoxal HCl, is from 1 µM to 10 µM.

13. The method of claim 12, wherein the cell culture medium comprises tetracaine HCL in a concentration of from 1 µM to 10 µM.

14. The method of claim 1, wherein the concentration of each of L-cysteinglutathione disulfide, γ-Glu-Cys, DL-kynurenine, D-penicillamine disulfide, phenacetin, phytosphingosine HCl, and pyridoxal HCl is 1 µM.

15. The method of claim 1, wherein the concentration of each of L-cysteinglutathione disulfide, γ-Glu-Cys, DL-kynurenine, D-penicillamine disulfide, phenacetin, phytosphingosine HCl, and pyridoxal HCl is 5 µM.

16. The method of claim 1, wherein the concentration of each of L-cysteinglutathione disulfide, γ-Glu-Cys, DL-kynurenine, D-penicillamine disulfide, phenacetin, phytosphingosine HCl, and pyridoxal HCl is 10 µM.

17. The method of claim 14, wherein the cell culture medium comprises tetracaine HCL in a concentration of 1 µM.

18. The method of claim 15, wherein the cell culture medium comprises tetracaine HCL in a concentration of 5 µM.

19. The method of claim 16, wherein the cell culture medium comprises tetracaine HCL in a concentration of 10 µM.

\* \* \* \* \*